(12) United States Patent
Fan et al.

(10) Patent No.: US 10,196,381 B2
(45) Date of Patent: Feb. 5, 2019

(54) BENZIMIDAZOLE-2-PIPERAZINE HETEROCYCLIC COMPOUND, PHARMACEUTICAL COMPOSITION CONTAINING THE SAME, PREPARATION METHOD AND USE THEREOF

(71) Applicant: Shanghai Huilun Life Science & Technology Co., Ltd., Shanghai (CN)

(72) Inventors: Xing Fan, Shanghai (CN); Jihong Qin, Shanghai (CN)

(73) Assignee: SHANGHAI HUILUN LIFE SCIENCE &TECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 14/898,658

(22) PCT Filed: Jun. 13, 2014

(86) PCT No.: PCT/CN2014/079827
§ 371 (c)(1),
(2) Date: Dec. 15, 2015

(87) PCT Pub. No.: WO2014/201972
PCT Pub. Date: Dec. 24, 2014

(65) Prior Publication Data
US 2016/0159776 A1  Jun. 9, 2016

(30) Foreign Application Priority Data

Jun. 17, 2013 (CN) .......................... 2013 1 0240069

(51) Int. Cl.
C07D 403/12 (2006.01)
C07D 401/12 (2006.01)

(52) U.S. Cl.
CPC ......... *C07D 403/12* (2013.01); *C07D 401/12* (2013.01)

(58) Field of Classification Search
None
See application file for complete search history.

(56) References Cited

U.S. PATENT DOCUMENTS

2007/0265324 A1    11/2007   Wernet et al.

FOREIGN PATENT DOCUMENTS

| CN | 1195985 A | 10/1998 |
|----|-----------|---------|
| CN | 1353695 A | 6/2002 |
| CN | 1425665 A | 6/2003 |
| CN | 1446218 A | 10/2003 |
| CN | 1486984 A | 4/2004 |
| CN | 101754967 A | 6/2010 |
| DE | 19920936 A1 | 11/2000 |
| WO | 2003106430 A1 | 12/2003 |

OTHER PUBLICATIONS

Australian Office Action issued in corresponding AU Application No. 2014283879 dated May 24, 2016.
International Search Report in corresponding PCT Application No. PCT/CN2014/079827 dated Sep. 23, 2014.

*Primary Examiner* — Marcos L Sznaidman
*Assistant Examiner* — Rayna Rodriguez
(74) *Attorney, Agent, or Firm* — Andrus Intellectual Property Law, LLP

(57) ABSTRACT

The present invention relates to a class of benzimidazole-2-piperazine heterocyclic derivatives, a preparation method and medical use thereof. Specifically, the present invention relates to a new benzimidazole-2-piperazine heterocyclic derivative of general Formula (I), a preparation method, a pharmaceutical composition containing the same, and use thereof as a therapeutic agent and especially as a poly(ADP-ribose)polymerase (PARP) inhibitor.

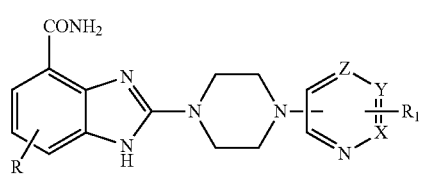

(I)

4 Claims, No Drawings

BENZIMIDAZOLE-2-PIPERAZINE HETEROCYCLIC COMPOUND, PHARMACEUTICAL COMPOSITION CONTAINING THE SAME, PREPARATION METHOD AND USE THEREOF

CROSS-REFERENCE TO RELATED APPLICATIONS

This application is the U.S. national stage application of International Application PCT/CN2014/079827, filed Jun. 13, 2014, which international application was published on Dec. 24, 2014, as International Publication WO2014/201972 in the Chinese language. The international application is incorporated herein by reference, in entirety. The international application claims priority to CN Patent Application No. 201310240069.7, filed Jun. 17, 2013, which is incorporated herein by reference, in entirety.

TECHNICAL FIELD

The present invention relates to a benzimidazole-2-piperazine heterocyclic compound, a preparation method, a pharmaceutical composition containing the same, and use thereof as a therapeutic agent and a poly(ADP-ribose) polymerase (PARP) inhibitor.

RELATED ART

Chemotherapeutics and ionizing radiation are two ways commonly used in the treatment of cancers. The two therapies both cause DNA single strand and/or double strand break, and thus exert a cytotoxic effect, resulting in the death of target tumor cells due to chromosome damage. In response to DNA damage, an important consequence is the activation of cell cycle checkpoint signaling for the purpose of protecting the cells against mitosis in case of DNA damage, thereby avoiding cell damage. In most cases, the tumor cells have a high proliferation rate while exhibiting deficiency in cell cycle checkpoint signaling. Therefore, it can be inferred that a specific mechanism of DNA repair exists in the tumor cells, which may rapidly respond to and repair the chromosome damage associated with proliferation regulation, such that the tumor cells survive the cytotoxic effect of some therapeutic agent.

In clinical use, the concentration of the chemotherapeutic agent or the intensity of the radiation is effective for counteracting the mechanism of DNA repair, to ensure the killing effect on target tumor cells. However, resistance to treatment may be developed in the tumor cells through a strengthened mechanism of DNA damage repair, such that the tumor cells survive the fatal DNA damage. To overcome the resistance development, the dose of the therapeutic agent or the intensity of the radiation is generally required to be enhanced. This has a detrimental effect on normal tissues around the lesion, whereby serious adverse effects are implicated during treatment, and the treatment risk is increased. Meanwhile, the therapeutic effect is decreased with increasing resistance. Therefore, it can be inferred that the cytotoxic effect of a DNA damaging agent may be improved in a tumor cell-specific manner by regulating the DNA damage signaling and repair mechanism.

Poly(ADP-ribose)polymerases (PARPs) characterized by poly(ADP-ribosyl)ation activity constitute a super family of 18 intranuclear and cytoplasmic enzymes. Through this poly(ADP-ribosyl)ation, the catalytic activity of target proteins and the protein-protein interactions may be modulated, and some fundamental biological processes are regulated, including DNA repair, and cell death. Moreover, the genomic stability also correlates with the poly(ADP-ribosyl)ation.

PARP-1 activity accounts for about 80% of the total PARP activity in the cells. PARP-1 and PARP-2 closest thereto are members in the PARP family that have an ability to repair the DNA damage. As a sensor and signaling protein of DNA damage, PARP-1 can quickly detect and directly bind to the site of DNA damage, followed by inducing the aggregation of numerous proteins required for DNA repair, such that the DNA damage is repaired. When PARP-1 is deficient in the cells, PARP-2 is able to repair the DNA damage in place of PARP-1. Studies show that compared with normal cells, PARPs are expressed at a generally increased level in solid tumors. Furthermore, cancers (e.g. breast and ovary cancer) which are deficient in DNA repair-related genes (e.g. BRCA-1 or BRCA-2) are extremely sensitive to the PARP-1 inhibitor, indicating that the PARP inhibitor, as a single therapeutic agent, is potentially useful in the treatment of triple negative breast cancer. Moreover, since the mechanism of DNA damage repair is a principal mechanism through which resistance is developed in the tumor cells counteracting the chemotherapeutic agent and ionizing radiation. Accordingly, PARP-1 is considered to be a target of interest in seeking a new method for treating cancers.

The PARP inhibitors that are developed and designed previously are analogues developed with nicotinamide of NAD that is a substrate for PARP as a template. These inhibitors are competitive inhibitors of NAD, which compete with NAD for the catalytic sites of PARP, thereby hindering the synthesis of poly(ADP-ribose) chain. Without the modification with poly(ADP-ribosyl)ation, PARP cannot be cleaved from the site of DNA damage, such that other proteins involved in repair cannot access the site of damage and thus the repair process cannot be performed. Therefore, under attack of cytotoxic agents or radiation, the presence of the PARP inhibitor ultimately leads to the death of tumor cells with impaired DNA.

In addition, NAD, consumed as a substrate for PARP, is essential to the synthesis of ATP in cells. At a high level of PARP activity, the intracellular NAD level decreases dramatically, thus affecting the ATP level in cells. Due to the inadequate content of ATP in the cells, the cells are failed in ATP-dependent programmed cell death, and have to turn to necrosis, a special apoptosis process. During necrosis, a large amount of inflammatory factors are released, causing a toxic effect to other organs and tissues. Therefore, the PARP inhibitor may find use in the treatment of many diseases associated with such a mechanism, including neurodegenerative diseases (for example, senile dementia, Huntington's disease, and Parkinson's disease), diabetes, ischemia or complications during ischemic reperfusion, for example, myocardial infarction and acute renal failure, diseases of circulatory system, for example, septic shock, and inflammatory diseases such as chronic rheumatism.

SUMMARY

An objective of the present invention is to provide a new benzimidazole-2-piperazine heterocyclic compound and a derivative thereof, as well as their tautomers, enantiomers, diastereomers, racemates, pharmaceutically acceptable salts, metabolites and metabolic precursors or prodrugs.

Another objective of the present invention is to provide a pharmaceutical composition comprising the benzimidazole-2-piperazine heterocyclic compound as an active ingredient.

A further objective of the present invention is to provide a method for preparing the benzimidazole-2-piperazine heterocyclic compound.

A still further objective of the present invention is to provide use of the benzimidazole-2-piperazine heterocyclic compound in the preparation of drugs.

In a first aspect of the present invention, a benzimidazole-2-piperazine heterocyclic compound of general Formula (I) is provided:

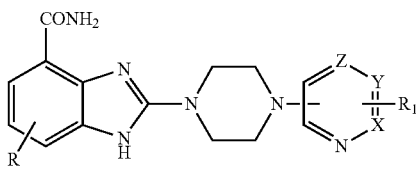

(I)

where in general Formula (I), R is hydrogen or halo;

one of X, Y, and Z is nitrogen, and the others are CH or X, Y, and Z are all CH;

$R_1$ is hydrogen, $C_1$-$C_6$ alkyl, methoxy, trifluoromethyl, halo, nitro, cyano, $CONR_2R_3$, and $NR_2R_3$;

$R_2$ is hydrogen, or $C_1$-$C_6$ alkyl; and $R_3$ is hydrogen, $C_1$-$C_6$ alkyl, or $C_3$-$C_6$ cycloalkyl, or $NR_2R_3$ are cyclized to form morpholinyl, tetrahydropyrrolyl, and piperidinyl.

Further preferably, in the compound of general Formula (I) provided in the present invention, R is hydrogen or fluoro;

one of X, Y, and Z is nitrogen, and the others are CH, or X, Y, and Z are all CH;

$R_1$ is hydrogen, $C_1$-$C_4$ alkyl, methoxy, trifluoromethyl, fluoro, nitro, cyano, $CONR_2R_3$, and $NR_2R_3$;

$R_2$ is hydrogen, or $C_1$-$C_4$ alkyl; and $R_3$ is hydrogen, $C_1$-$C_4$ alkyl, or $C_3$-$C_6$ cycloalkyl, or $NR_2R_3$ are cyclized to form morpholinyl, and tetrahydropyrrolyl.

Most preferably, the compound of general Formula (I) according to the present invention is Compounds (1)-(37) below:

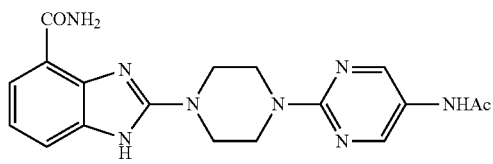

(1)

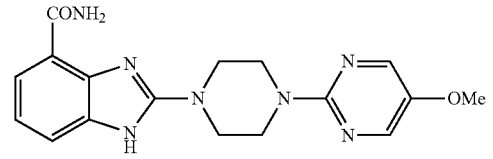

(2)

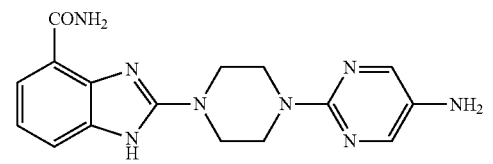

(3)

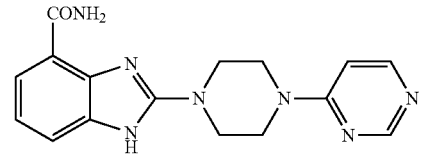

(4)

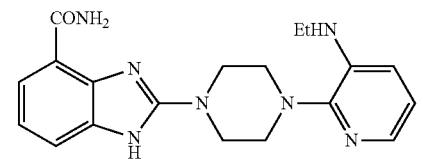

(5)

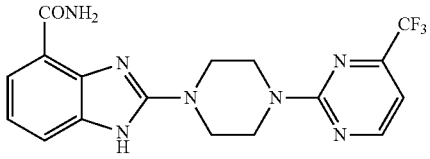

(6)

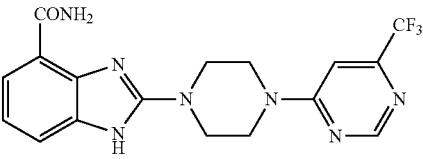

(7)

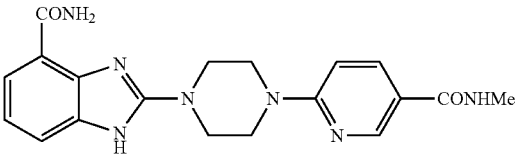

(8)

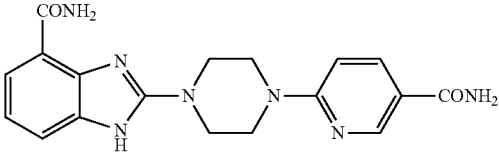

(9)

(10)

(11)

(12)

-continued (13)(14)(15)(16)(17)(18)(19)(20)(21)(22)(23)(24)(25)(26)(27)(28)(29)

(30)
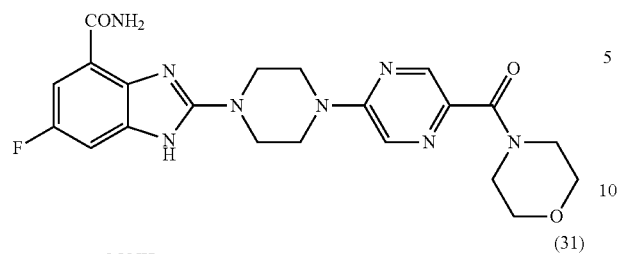

(31)
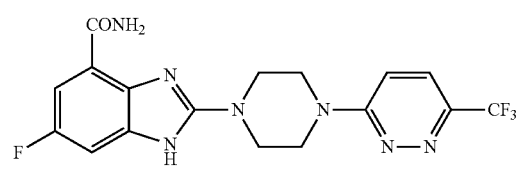

(32)
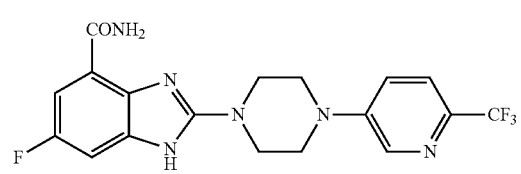

(33)
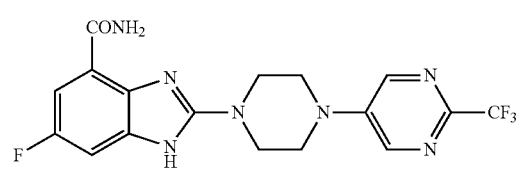

(34)
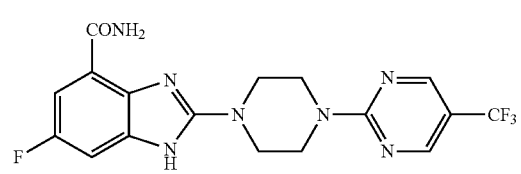

(35)
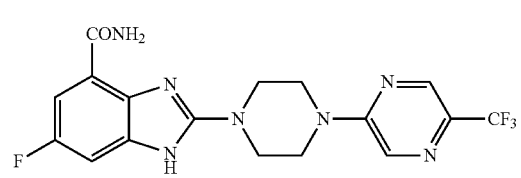

(36)
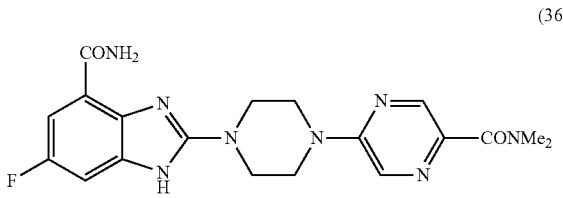

(37)
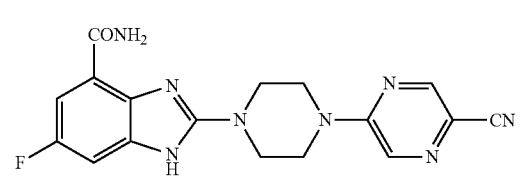

(38)
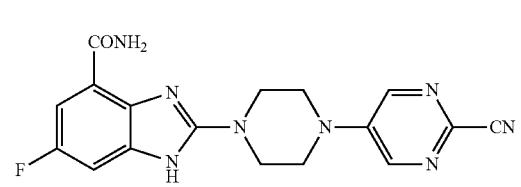

(39)
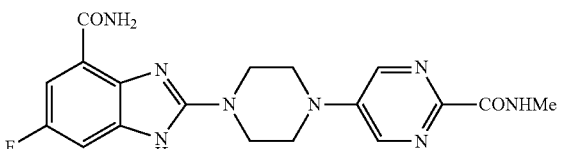

(40)
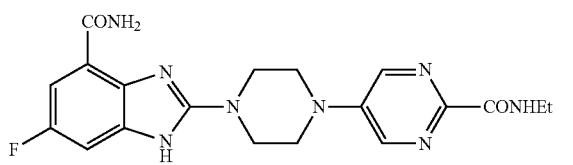

(41)
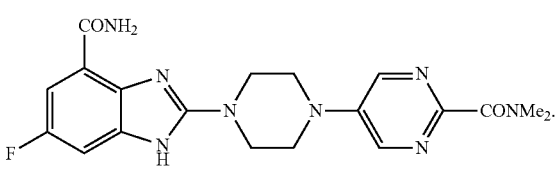

The compound of general Formula (I) is any one of an enantiomer, a diastereoisomer, and a conformer, or a mixture of two or more thereof.

The compound of general Formula (I) is a pharmaceutically acceptable derivative.

The compound of general Formula (I) according to the present invention may exist as a pharmaceutically acceptable salt.

The pharmaceutically acceptable salt according to the present invention is a hydrochloride, a sulfate, a phosphate, an acetate, a trifluoroacetate, a methanesulfonate, a trifluoromethanesulfonate, a p-toluenesulfonate, a tartrate, a maleate, a fumarate, a succinate or a malate of the compound of general Formula (I).

In a preferred embodiment of the present invention, the benzimidazole-2-piperazine heterocyclic compound of general Formula (I) is a 2-(piperazin-1-yl)-1H-benzimidazole-4-carboxamide compound and a pharmaceutically acceptable salt thereof.

In a second aspect of the present invention, a method for preparing the compound of general Formula (I) is provided. The reaction scheme is as follows:

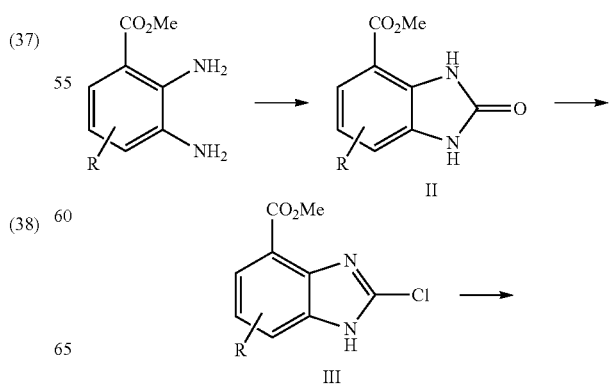

-continued

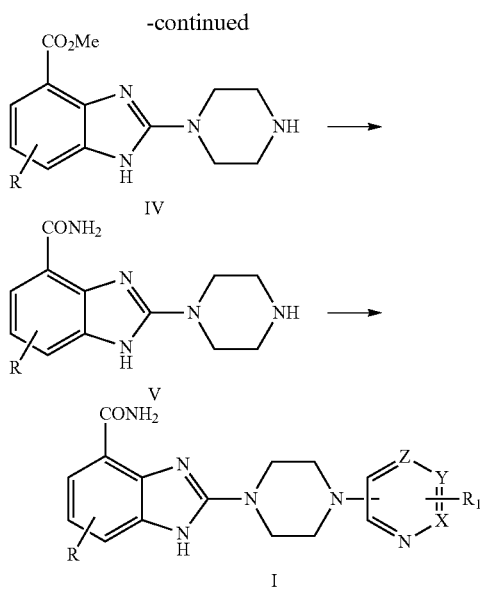

where R and $R_1$ are as defined above. The method comprises specifically:

Step 1): cyclizing substituted methyl 2,3-diaminobenzoate with carbonyldiimidazole, to obtain substituted methyl 2-oxo-2,3-dihydro-1H-benzimidazole-4-carboxylate (II);

Step 2): chlorinating the substituted methyl 2-oxo-2,3-dihydro-1H-benzimidazole-4-carboxylate (II) obtained in Step 1) through reaction with phosphorus oxychloride, to obtain substituted methyl 2-chloro-1H-benzimidazole-4-carboxylate (III);

Step 3): subjecting the substituted methyl 2-chloro-1H-benzimidazole-4-carboxylate (III) obtained in Step 2) to nucleophilic substitution with piperazine in the presence of a base, to obtain substituted methyl 2-(piperazin-1-yl)-1H-benzimidazole-4-carboxylate (IV);

Step 4): aminolyzing the ester group of the substituted methyl 2-(piperazin-1-yl)-1H-benzimidazole-4-carboxylate (IV) obtained in Step 3) in a methanolic ammonia solution, to obtain substituted 2-(piperazin-1-yl)-1H-benzimidazole-4-carboxamide (V); and Step 5): coupling the substituted 2-(piperazin-1-yl)-1H-benzimidazole-4-carboxamide (V) obtained in Step 4) with an acid, or reductively aminating the substituted 2-(piperazin-1-yl)-1H-benzimidazole-4-carboxamide (V) obtained in Step 4) with an aldehyde, to generate the compound of general Formula (I).

In a third aspect, a pharmaceutical composition is provided, which comprises a therapeutically effective amount of the compound of general Formula (I) as the active ingredient and one or more pharmaceutically acceptable carriers and/or diluents, or comprises a therapeutically effective amount of the compound of general Formula (I) as the active ingredient and a pharmaceutically acceptable carrier, excipient, or diluent.

In the third aspect, a pharmaceutical composition is provided, which comprises a therapeutically effective amount of a pharmaceutically acceptable derivative of the compound of general Formula (I) as the active ingredient and one or more pharmaceutically acceptable carriers and/or diluents, or comprises a therapeutically effective amount of a pharmaceutically acceptable derivative of the compound of general Formula (I) as the active ingredient and a pharmaceutically acceptable carrier, excipient, or diluent.

In the third aspect, a pharmaceutical composition is provided, which comprises a therapeutically effective amount of a pharmaceutically acceptable salt of the compound of general Formula (I) as the active ingredient and one or more pharmaceutically acceptable carriers and/or diluents, or comprises a therapeutically effective amount of a pharmaceutically acceptable salt of the compound of general Formula (I) as the active ingredient and a pharmaceutically acceptable carrier, excipient or diluent.

The pharmaceutical composition may be prepared into tablets, capsules, an aqueous suspension, an oily suspension, a dispersible powder, granules, lozenges, an emulsion, a syrup, a cream, an ointment, a suppository or an injection.

In the pharmaceutical composition, the compound of general Formula (I) may exist in free form.

In a fourth aspect of the present invention, use of the compound of general Formula (I) in the preparation of drugs for treating diseases that are ameliorated through inhibition of the PARP activity is provided.

In the fourth aspect of the present invention, use of a pharmaceutically acceptable derivative of the compound of general Formula (I) in the preparation of drugs for treating diseases that are ameliorated through inhibition of the PARP activity is provided.

In the fourth aspect of the present invention, use of a pharmaceutically acceptable salt of the compound of general Formula (I) in the preparation of drugs for treating diseases that are ameliorated through inhibition of the PARP activity is provided.

In the fourth aspect of the present invention, use of the pharmaceutical composition in the preparation of drugs for treating diseases that are ameliorated through inhibition of the PARP activity is provided.

The diseases that are ameliorated through inhibition of the PARP activity include vascular diseases, septic shock, ischemic damage, neurotoxic symptoms, hemorrhagic shock, inflammatory disease or multiple sclerosis.

In the fourth aspect of the present invention, use of the compound of general Formula (I) in the preparation of adjuvant drugs for treating tumors is provided.

In the fourth aspect of the present invention, use of a pharmaceutically acceptable derivative of the compound of general Formula (I) in the preparation of adjuvant drugs for treating tumors is provided.

In the fourth aspect of the present invention, use of a pharmaceutically acceptable salt of the compound of general Formula (I) in the preparation of adjuvant drugs for treating tumors is provided.

In the fourth aspect of the present invention, use of the pharmaceutical composition in the preparation of adjuvant drugs for treating tumors is provided.

In the fourth aspect of the present invention, use of the compound of general Formula (I) in the preparation of drugs for boosting tumor radiotherapy is provided.

In the fourth aspect of the present invention, use of a pharmaceutically acceptable derivative of the compound of general Formula (I) in the preparation of drugs for boosting tumor radiotherapy is provided.

In the fourth aspect of the present invention, use of a pharmaceutically acceptable salt of the compound of general Formula (I) in the preparation of drugs for boosting tumor radiotherapy is provided.

In the fourth aspect of the present invention, use of the pharmaceutical composition in the preparation of drugs for boosting tumor radiotherapy is provided.

In the fourth aspect of the present invention, use of the compound of general Formula (I) in the preparation of chemotherapeutic agents for tumors is provided.

In the fourth aspect of the present invention, use of a pharmaceutically acceptable derivative of the compound of general Formula (I) in the preparation of chemotherapeutic agents for tumors is provided.

In the fourth aspect of the present invention, use of a pharmaceutically acceptable salt of the compound of general Formula (I) in the preparation of chemotherapeutic agents for tumors is provided.

In the fourth aspect of the present invention, use of the pharmaceutical composition in the preparation of chemotherapeutic agents for tumors is provided.

In the fourth aspect of the present invention, use of the compound of general Formula (I) in the preparation of drugs for treating an individual with a cancer which is deficient in Homologous Recombination (HR) dependent DNA double strand break (DSB) repair is provided.

In the fourth aspect of the present invention, use of a pharmaceutically acceptable derivative of the compound of general Formula (I) in the preparation of drugs for treating an individual with a cancer which is deficient in Homologous Recombination (HR) dependent DNA double strand break (DSB) repair is provided.

In the fourth aspect of the present invention, use of a pharmaceutically acceptable salt of the compound of general Formula (I) in the preparation of drugs for treating an individual with a cancer which is deficient in Homologous Recombination (HR) dependent DNA double strand break (DSB) repair is provided.

In the fourth aspect of the present invention, use of the pharmaceutical composition in the preparation of drugs for treating an individual with a cancer which is deficient in Homologous Recombination (HR) dependent DNA double strand break (DSB) repair is provided.

Preferably, the cancer comprises one or more cancer cells having a reduced or abrogated ability to repair DNA DSB by HR relative to normal cells.

Preferably, the cancer has a BRCA-1 or BRCA-2 deficient mutant phenotype.

Preferably, the cancer is breast, ovary, pancreas or prostate cancer.

To examine the degree of inhibition of the compounds provided in the present invention on the PARP enzyme, the activity of the compounds of the present invention for PARP enzyme are determined through biological enzyme activity assay.

PARP is an enzyme responsible for post-translational modification, which may be activated by means of DNA damage. The process catalyzed by PARP in vivo is mainly NAD-dependent poly(ADP-ribosyl)ation, in which the substrates are mainly some nuclear proteins including PARP, one example of which is histone. In the present invention, the PARP activity is assayed by determining the poly(ADP-ribosyl)ation degree of histone coated in a 96-well plate in the presence of NAD, and the PARP activity under the action of a PARP inhibitor is correspondingly assayed, thereby evaluating the degree of inhibition of the compounds on PARP activity.

DETAILED DESCRIPTION

The terms used in the description and claims have the following meanings, unless stated otherwise.

In the present invention, the term "$C_1$-$C_6$ alkyl" refers to a saturated linear or branched monovalent hydrocarbyl group having 1 to 6 carbon atoms. Examples include, but are not limited to, methyl, ethyl, propyl, isopropyl, n-butyl, iso-butyl, and t-butyl.

The term "halogen" and "halo" refer to F, Cl, Br, and I.

"Pharmaceutically acceptable salt" refers to a salt that retains the biological effectiveness and properties of the parent compound. The salt includes:

(1) acid addition salts, obtainable through reaction of the parent compound as a free base with an inorganic acid including hydrochloric, hydrobromic, nitric, phosphoric, metaphosphoric, sulfuric, sulfurous, perchloric acid and the like; or an organic acid including acetic, propionic, acrylic, oxalic, (d) or (L)-malic, fumaric, maleic, hydroxybenzoic, γ-hydroxybutyric, methoxybenzoic, phthalic, methanesulfonic, ethanesulfonic, naphthalene-1-sulfonic, naphthalene-2-sulfonic, p-toluenesulfonic, salicylic, tartaric, citric, lactic, mandelic, succinic or malonic acid; or (2) salts formed by replacing the acidic proton present in the parent compound with a metal ion, for example, alkali metal ion, alkaline earth metal ion or aluminum ion; or through coordination with an organic base, for example, ethanolamine, diethanolamine, triethanolamine, tromethamine, N-methyl glucosamine, and the like.

"Pharmaceutical composition" refers to a mixture of one or more of the compound according to the present invention or a pharmaceutically acceptable salt, solvate, hydrate or prodrug thereof with other chemical ingredients, for example, a pharmaceutically acceptable carrier. The pharmaceutical composition is provided for the purpose of promoting the administration of the drug to an animal.

"Pharmaceutically acceptable carrier" refers to an inactive ingredient in the pharmaceutical composition that does not cause significant irritation to an organism and does not interfere with the biological activity and properties of the administered compound, for example, but not limited to: calcium carbonate, calcium phosphate, various carbohydrates (e.g. lactose, and mannitol), starch, cyclodextrin, magnesium stearate, cellulose, magnesium carbonate, acrylic polymers or methacrylic polymers, gel, water, polyethylene glycol, propylene glycol, ethylene glycol, castor oil, hydrogenated castor oil or polyethoxyhydrogenated castor oil, sesame oil, corn oil, and peanut oil.

In addition to the pharmaceutically acceptable carrier, the pharmaceutical composition may further comprises pharmaceutically acceptable adjuvants, for example antibacterial agents, antifungal agents, antimicrobial agents, preservatives, colorants, solubilizers, thickeners, surfactants, chelating agents, proteins, amino acids, lipids, carbohydrates, vitamins, minerals, trace elements, sweeteners, pigments, fragrances or a combination thereof.

In the present invention, a compound and use of the compound as a poly(ADP-ribose)polymerase inhibitor are provided. The process parameters may be appropriately adapted by those skilled in the art based on the disclosures herein. It should be particularly noted that all equivalent replacements and modifications are apparent to those skilled in the art, and contemplated by the present invention. The method and use of the present invention have been described with reference to preferred examples, and it is apparent that the invention may be implemented and applied by persons of skill in the art through modification, or appropriate alternation and combination made to the method and use of the present invention without departing from the disclosures, spirits and scope of the present invention.

Hereinafter, the present invention is further described with reference to examples.

PREPARATION EXAMPLES

Example 1

Preparation of Compound (1): 2-(4-(pyrimidin-2-yl)piperazin-1-yl)-1H-benzimidazole-4-carboxamide The reaction scheme was specifically as follows.

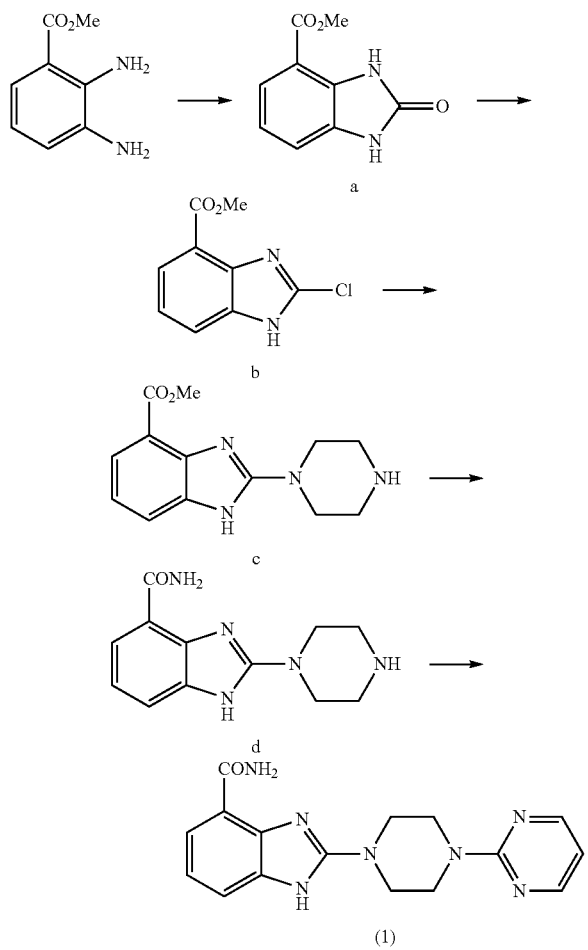

Step 1: Preparation of methyl 2-oxo-2,3-dihydro-1H-benzimidazole-4-carboxylate

To a solution of methyl 2,3-diaminobenzoate (0.8 g, 4.8 mmol) dissolved in anhydrous tetrahydrofuran (20 mL), carbonyldiimidazole (1.56 g, 9.6 mmol) was added, warmed to reflux, and reacted for 8 hrs. After cooling, the solvent was removed under reduced pressure, and the residue was separated by flash column chromatography (petroleum ether: ethyl acetate=5:1) to obtain Compound a: methyl 2-oxo-2, 3-dihydro-1H-benzimidazole-4-carboxylate as a light solid (0.3 g, yield 33%). MS (ESI) m/z: [M+H]$^+$=193.

Step 2: Preparation of methyl 2-chloro-1H-benzimidazole-4-carboxylate

Compound a: methyl 2-oxo-2,3-dihydro-1H-benzimidazole-4-carboxylate (1.1 g, 5.7 mmol) was added to phosphorus oxychloride (8 mL), warmed to reflux, and reacted for 8 hrs. After cooling, the solvent was removed under reduced pressure, and the residue was separated by flash column chromatography (petroleum ether:ethyl acetate=5:1) to obtain Compound b: methyl 2-chloro-1H-benzimidazole-4-carboxylate as a white solid (1.5 g, yield 100%). MS (ESI) m/z: [M+H]$^+$=211.

Step 3: Preparation of methyl 2-(piperazin-1-yl)-1H-benzimidazole-4-carboxylate

To Compound b: methyl 2-chloro-1H-benzimidazole-4-carboxylate (59 mg, 0.28 mmol) dissolved in dimethylformamide (5 mL), piperazine (110 mg, 1.12 mmol) was added, warmed to 100° C., and reacted for 8 hrs. After cooling, the solvent was removed under reduced pressure, and the residue was separated by flash column chromatography (dichloromethane:methanol=10:1) to obtain Compound c: methyl 2-(piperazin-1-yl)-1H-benzimidazole-4-carboxylate as a white solid (100 mg, yield 100%). MS (ESI) m/z: [M+H]$^+$=261.

Step 4: Preparation of 2-(piperazin-1-yl)-1H-benzimidazole-4-carboxamide

To a solution of Compound c: methyl 2-(piperazin-1-yl)-1H-benzimidazole-4-carboxylate (100 mg, 0.28 mmol) dissolved in tetrahydrofuran (5 mL), aqueous ammonia (5 mL) was added, warmed to 70° C., sealed, and reacted for 8 hrs. After cooling, the solvent was removed under reduced pressure, and the residue was separated by flash column chromatography (dichloromethane:methanol=10:1) to obtain Compound d: 2-(piperazin-1-yl)-1H-benzimidazole-4-carboxamide as a white solid (20 mg, yield 28%). MS (ESI) m/z: [M+H]$^+$=246.

Step 5: Preparation of 2-(4-(pyrimidin-2-yl)piperazin-1-yl)-1H-benzimidazole-4-carboxamide To Compound d: 2-(piperazin-1-yl)-1H-benzimidazole-4-carboxamide (74 mg, 0.3 mmol) dissolved in dimethylformamide (5 mL), 2-chloropyrimidine (34 mg, 0.3 mmol) and triethylamine (30 mg, 0.3 mmol) were added, warmed to 100° C., and reacted for 8 hrs. After cooling, the solvent was removed under reduced pressure, and the residue was separated by flash column chromatography (dichloromethane: methanol=10:1) to obtain Compound (1): 2-(4-(pyrimidin-2-yl)piperazin-1-yl)-1H-benzimidazole-4-carboxamide (32 mg, yield 33%). LC-MS (ESI): m/z 324 (M+1)$^+$. $^1$H NMR (300 MHz, DMSO-d6): δ 12.10 (br, 1H), 9.16 (br, 1H), 8.44-8.38 (m, 2H), 7.62-7.54 (m, 2H), 7.36-7.32 (m, 1H), 7.01-6.95 (m, 1H), 6.70-6.63 (m, 1H), 3.89 (br, 4H), 3.67 (br, 4H).

Example 2

Preparation of Compound (2) 2-(4-(5-fluoropyrimidin-2-yl)piperazin-1-yl)-1H-benzimidazole-4-carboxamide

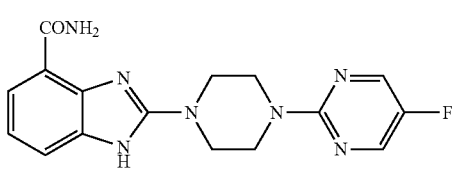

(2)

Analogous to the process in Step 5 in Preparation of Compound (1) in Example 1, Compound d: 2-(piperazin-1-yl)-1H-benzimidazole-4-carboxamide was subjected to aromatic nucleophilic substitution with 2-chloro-5-fluoropyrimidine, to obtain Compound (2): 2-(4-(5-fluoropyrimidin-2-yl)piperazin-1-yl)-1H-benzimidazole-4-carboxamide (30 mg, yield 72%). LC-MS (ESI): m/z 342 (M+1)+. $^1$H NMR (300 MHz, DMSO-d6): δ 11.92 (br, 1H), 9.13 (br, 1H), 8.50 (s, 2H), 7.60 (d, 1H, J=7.8 Hz), 7.52 (br, 1H), 7.32 (d, 1H, J=7.8 Hz), 6.98 (t, 1H, J=7.8 Hz), 3.87-3.83 (m, 4H), 3.67-3.64 (m, 4H).

Example 3

Preparation of Compound (3): 2-(4-(5-ethylaminopyrimidin-2-yl)piperazin-1-yl)-1H-benzimidazole-4-carboxamide

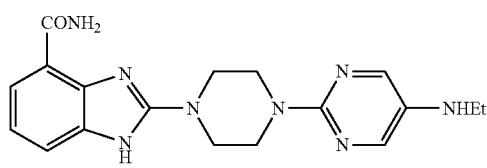

(3)

Analogous to the process in Step 5 in Preparation of Compound (1) in Example 1, Compound d: 2-(piperazin-1-yl)-1H-benzimidazole-4-carboxamide was subjected to aromatic nucleophilic substitution with 2-chloro-5-ethylaminopyrimidine, to obtain Compound (3): 2-(4-(5-ethylaminopyrimidin-2-yl)piperazin-1-yl)-1H-benzimidazole-4-carboxamide (23 mg, yield 42%). LC-MS (ESI): m/z 367 (M+1)+. $^1$H NMR (300 MHz, DMSO-d6): δ 9.08 (br, 1H), 7.92 (s, 2H), 7.78-7.72 (m, 2H), 7.66-7.60 (m, 2H), 7.22-7.16 (m, 1H), 4.71-4.67 (m, 2H), 4.19-4.15 (m, 2H), 3.73-3.70 (m, 4H), 2.65-2.60 (m, 2H), 1.37 (t, 3H, J=4.5 Hz).

Example 4

Preparation of Compound (4): 2-(4-(5-acetamidopyrimidin-2-yl)piperazin-1-yl)-1H-benzimidazole-4-carboxamide

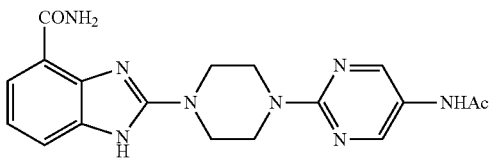

(4)

Analogous to the process in Step 5 in Preparation of Compound (1) in Example 1, Compound d: 2-(piperazin-1-yl)-1H-benzimidazole-4-carboxamide was subjected to aromatic nucleophilic substitution with 2-chloro-5-acetamidopyrimidine, to obtain Compound (4): 2-(4-(5-acetamidopyrimidin-2-yl)piperazin-1-yl)-1H-benzimidazole-4-carboxamide (12 mg, yield 22%). LC-MS (ESI): m/z 381 (M+1)+. $^1$H NMR (300 MHz, DMSO-d6): δ 11.85 (br, 1H), 9.89 (br, 1H), 9.14 (s, 1H), 8.54 (s, 2H), 7.60 (d, 1H, J=7.5 Hz), 7.51 (br, 1H), 7.31 (d, 1H, J=7.5 Hz), 6.98 (t, 1H, J=7.5 Hz), 3.84-3.65 (m, 8H), 2.00 (s, 3H).

Example 5

Preparation of Compound (5): 2-(4-(5-methoxypyrimidin-2-yl)piperazin-1-yl)-1H-benzimidazole-4-carboxamide

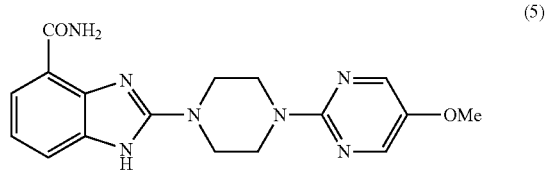 [SMILES: COc1cnc(N2CCN(c3nc4c(C(N)=O)cccc4[nH]3)CC2)nc1]

(5)

Analogous to the process in Step 5 in Preparation of Compound (1) in Example 1, Compound d: 2-(piperazin-1-yl)-1H-benzimidazole-4-carboxamide was subjected to aromatic nucleophilic substitution with 2-chloro-5-methoxypyrimidine, to obtain Compound (5): 2-(4-(5-methoxypyrimidin-2-yl)piperazin-1-yl) 1H-benzimidazole-4-carboxamide (17 mg, yield 41%). LC-MS (ESI): m/z 354 (M+1)+. $^1$H NMR (300 MHz, DMSO-d6): δ 11.86 (br, 1H), 9.15 (br, 1H), 8.25 (s, 2H), 7.60 (d, 1H, J=7.5 Hz), 7.51 (br, 1H), 7.31 (d, 1H, J=7.5 Hz), 6.98 (t, 1H, J=7.5 Hz), 3.77 (br, 7H), 3.64 (br, 4H).

Example 6

Preparation of Compound (6): 2-(4-(5-aminopyrimidin-2-yl)piperazin-1-yl)-1H-benzimidazole-4-carboxamide

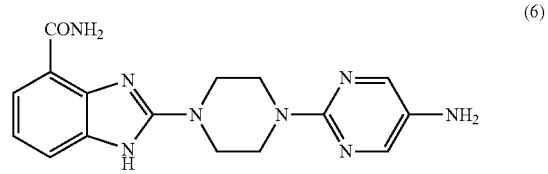 [SMILES: NC(=O)c1cccc2[nH]c(N3CCN(c4ncc(N)cn4)CC3)nc12]

(6)

Analogous to the process in Step 5 in Preparation of Compound (1) in Example 1, Compound d: 2-(piperazin-1-yl)-1H-benzimidazole-4-carboxamide was subjected to aromatic nucleophilic substitution with 2-chloro-5-aminopyrimidine, to obtain Compound (6): 2-(4-(5-aminopyrimidin-2-yl)piperazin-1-yl)-1H-benzimidazole-4-carboxamide (190 mg, yield 83%). LC-MS (ESI): m/z 339 (M+1)+. $^1$H NMR (300 MHz, DMSO-d6): δ 9.12 (br, 1H), 7.60-7.25 (m, 7H), 7.00-6.95 (m, 1H), 3.67 (br, 8H).

Example 7

Preparation of Compound (7): 2-(4-(pyrimidin-4-yl)piperazin-1-yl)-1H-benzimidazole-4-carboxamide

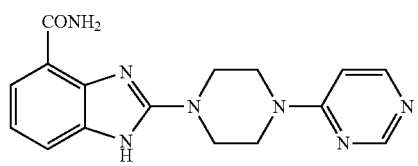

(7)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 4-chloropyrimidine, to obtain Compound (7): 2-(4-(pyrimidin-4-yl)piperazin-1-yl)-1H-benzimidazole-4-carboxamide (25 mg, yield 65%). LC-MS (ESI): m/z 324 (M+1)⁺. $^1$H NMR (300 MHz, DMSO-d6): δ 11.85 (br, 1H), 9.09 (br, 1H), 8.53 (s, 1H), 8.22 (d, 1H, J=8.1 Hz), 7.60 (d, 1H, J=7.5 Hz), 7.50 (br, 1H), 7.33 (d, 1H, J=7.5 Hz), 6.99 (t, 1H, J=7.5 Hz), 6.91 (d, 1H, J=8.1 Hz), 3.80-3.79 (m, 4H), 3.68-3.66 (m, 4H).

Example 8

Preparation of Compound (8): 2-(4-(3-ethylaminopyridin-2-yl)piperazin-1-yl)-1H-benzimidazole-4-carboxamide

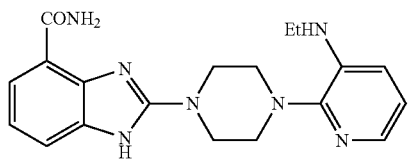

(8)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 2-chloro-3-ethylaminopyridine, to obtain Compound (8): 2-(4-(3-ethylaminopyridin-2-yl)piperazin-1-yl)-1H-benzimidazole-4-carboxamide (13 mg, yield 36%). LC-MS (ESI): m/z 366 (M+1)⁺. $^1$H NMR (300 MHz, DMSO-d6): δ 12.02 (br, 1H), 9.18 (br, 1H), 7.62-7.50 (m, 4H), 7.34-7.31 (m, 1H), 7.00-6.89 (m, 3H), 3.77-3.74 (m, 4H), 3.14-3.10 (m, 4H), 2.00-1.93 (m, 2H), 0.85-0.80 (m, 3H).

Example 9

Preparation of Compound (9): 2-(4-(4-trifluoromethylpyrimidin-2-yl)piperazin-1-yl)-1H-benzimidazole-4-carboxamide

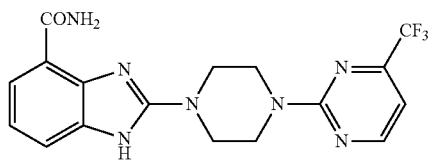

(9)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 2-chloro-4-trifluoromethylpyrimidine, to obtain Compound (9): 2-(4-(4-trifluoromethylpyrimidin-2-yl)piperazin-1-yl)-1H-benzimidazole-4-carboxamide (36 mg, yield 55%). LC-MS (ESI): m/z 392 (M+1)⁺. $^1$H NMR (300 MHz, DMSO-d6): δ 11.87 (br, 1H), 9.13 (br, 1H), 8.72 (d, 1H, J=4.8 Hz), 7.61 (d, 1H, J=7.8 Hz), 7.53 (br, 1H), 7.33 (d, 1H, J=7.8 Hz), 7.07 (d, 1H, J=4.8 Hz), 6.99 (t, 1H, J=7.8 Hz), 3.94 (br, 4H), 3.69 (br, 4H).

Example 10

Preparation of Compound (10): 2-(4-(6-trifluoromethylpyrimidin-4-yl)piperazin-1-yl)-1H-benzimidazole-4-carboxamide

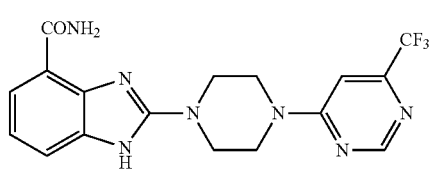

(10)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 6-chloro-4-trifluoromethylpyrimidine, to obtain Compound (10): 2-(4-(6-trifluoromethylpyrimidin-4-yl)piperazin-1-yl)-1H-benzimidazole-4-carboxamide (40 mg, yield 61%). LC-MS (ESI): m/z 392 (M+1)⁺. $^1$H NMR (300 MHz, DMSO-d6): δ 11.88 (br, 1H), 9.12 (br, 1H), 8.66 (s, 1H), 7.61 (d, 1H, J=7.5 Hz), 7.53 (br, 1H), 7.35 (s, 1H), 7.33 (d, 1H, J=7.5 Hz), 6.99 (t, 1H, J=7.5 Hz), 3.92 (br, 4H), 3.69 (br, 4H).

Example 11

Preparation of Compound (11): 2-(4-(5-methylcarbamoylpyridin-2-yl)piperazin-1-yl)-1H-benzimidazole-4-carboxamide

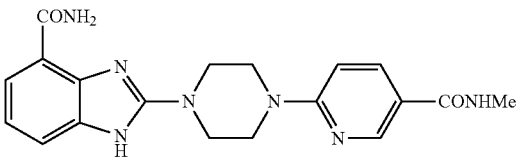

(11)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 6-chloro-3-methylcarbamoylpyridine, to obtain Compound (11): 2-(4-(5-methylcarbamoylpyridin-2-yl)piperazin-1-yl)-1H-benzimidazole-4-carboxamide (15 mg, yield 24%). LC-MS (ESI): m/z 380 (M+1)⁺. $^1$H NMR (300 MHz, DMSO-d6): δ 11.86 (br, 1H), 9.14 (br, 1H), 8.6 (s, 1H), 8.24 (br, 1H), 7.96 (d, 1H, J=9.6 Hz), 7.61 (d, 1H, J=7.8 Hz), 7.52 (br, 1H), 7.32 (d, 1H, J=7.8 Hz), 7.01-6.92 (m, 2H), 3.77 (br, 4H), 3.67 (br, 4H), 2.74 (d, 3H, d=4.2 Hz).

Example 12

Preparation of Compound (12): 2-(4-(5-carbamoylpyridin-2-yl)piperazin-1-yl)-1H-benzimidazole-4-carboxamide

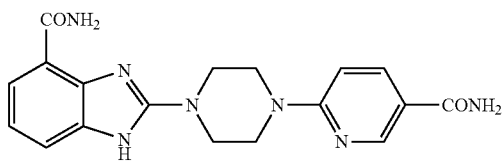

(12)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 6-chloro-3-carbamoylpyridine, to obtain Compound (12): 2-(4-(5-carbamoylpyridin-2-yl)piperazin-1-yl)-1H-benzimidazole-4-carboxamide (25 mg, yield 41%). LC-MS (ESI): m/z 366 (M+1)$^+$. $^1$H NMR (300 MHz, DMSO-d6): δ 11.86 (br, 1H), 9.14 (br, 1H), 8.64 (s, 1H), 7.99 (d, 1H, J=7.8 Hz), 7.79 (br, 1H), 7.60 (d, 1H, J=9.0 Hz), 7.51 (br, 1H), 7.32 (d, 1H, J=7.8 Hz), 7.17 (br, 1H), 7.01-6.91 (m, 2H), 3.78 (br, 4H), 3.67 (br, 4H).

Example 13

Preparation of Compound (13): 2-(4-(2-trifluoromethylpyridin-4-yl)piperazin-1-yl)-1H-benzimidazole-4-carboxamide

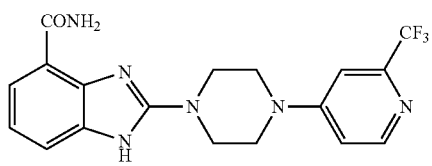

(13)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 4-chloro-2-trifluoromethylpyridine, to obtain Compound (13): 2-(4-(2-trifluoromethylpyridin-4-yl)piperazin-1-yl)-1H-benzimidazole-4-carboxamide (7 mg, yield 13%). LC-MS (ESI): m/z 391 (M+1)$^+$. $^1$H NMR (300 MHz, DMSO-d6): δ 11.88 (br, 1H), 9.13 (br, 1H), 8.34-8.29 (m, 1H), 7.63-7.60 (m, 1H), 7.53 (br, 1H), 7.35-7.30 (m, 2H), 7.12-7.09 (m, 1H), 7.03-6.97 (m, 1H), 3.70-3.64 (m, 8H).

Example 14

Preparation of Compound (14): 2-(4-(5-cyanopyrimidin-2-yl)piperazin-1-yl)-1H-benzimidazole-4-carboxamide

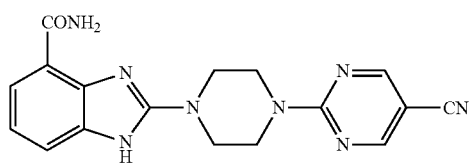

(14)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 2-chloro-5-cyanopyrimidine, to obtain Compound (14): 2-(4-(5-cyanopyrimidin-2-yl)piperazin-1-yl)-1H-benzimidazole-4-carboxamide (40 mg, yield 71%). LC-MS (ESI): m/z 349 (M+1)$^+$. $^1$H NMR (300 MHz, DMSO-d6): δ 11.88 (br, 1H), 9.09 (br, 1H), 8.80 (s, 2H), 7.60 (d, 1H, J=7.2 Hz), 7.53 (br, 1H), 7.33 (d, 1H, J=7.2 Hz), 6.99 (t, 1H, J=7.2 Hz), 4.01 (br, 4H), 3.69 (br, 4H).

Example 15

Preparation of Compound (15): 2-(4-(5-dimethylcarbamoylpyridin-2-yl)piperazin-1-yl)-1H-benzimidazole-4-carboxamide

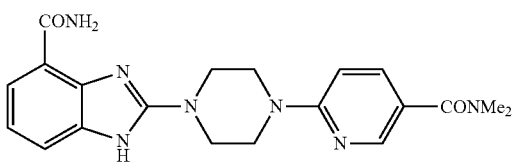

(15)

Analogous to the process in Step 5 in Preparation of Compound (1) in Example 1, Compound d: 2-(4-(pyrimidin-4-yl)piperazin-1-yl)-1H-benzimidazole-4-carboxamide was subjected to aromatic nucleophilic substitution with 6-chloro-3-dimethylcarbamoylpyridine, to obtain Compound (15): 2-(4-(5-dimethylcarbamoylpyridin-2-yl)piperazin-1-yl)-1H-benzimidazole-4-carboxamide (35 mg, yield 44%). LC-MS (ESI): m/z 394 (M+1)$^+$. $^1$H NMR (300 MHz, DMSO-d6): δ 12.11 (br, 1H), 9.19 (br, 1H), 8.24 (s, 1H), 7.66-7.59 (m, 2H), 7.53 (br, 1H), 7.34-7.31 (m, 1H), 7.00-6.91 (m, 2H), 3.73-3.70 (m, 8H), 2.96 (s, 6H).

Example 16

Preparation of Compound (16): 6-fluoro-2-(4-(pyrimidin-4-yl)piperazin-1-yl)-1H-benzimidazole-4-carboxamide The reaction scheme was specifically as follows

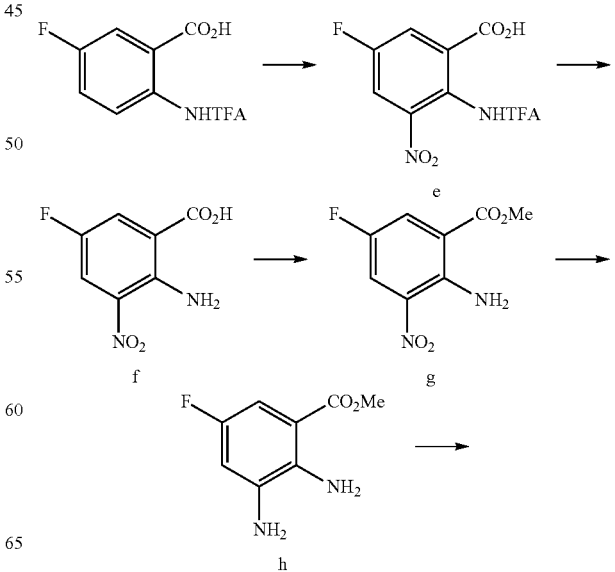

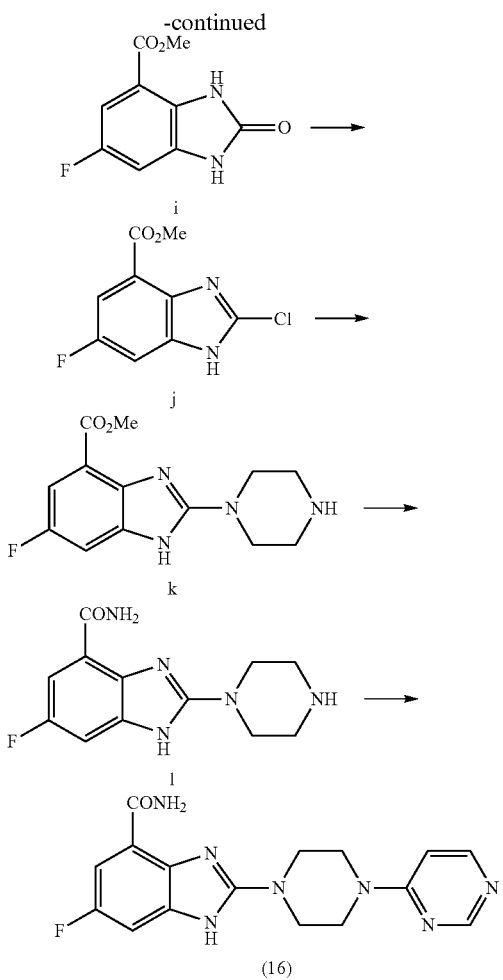

Step 1: Preparation of 5-fluoro-3-nitro-2-(2,2,2-trifluoroacetamido)benzoic acid 2-trifluoroacetamido-5-fluoro-benzoic acid (2.5 g, 10 mmol) was slowly added to fuming nitric acid (14 mL) while in an ice bath. The reaction was continued for 1 hr with stirring while in the ice bath, then poured into ice-water, and filtered, to obtain Compound e: 5-fluoro-3-nitro-2-(2,2,2-trifluoroacetamido)benzoic acid as a white solid (1.9 g, yield 65%). MS (ESI) m/z: $[M-H]^-=295$.

Step 2: Preparation of 2-amino-5-fluoro-3-nitrobenzoic acid

A 10% aqueous sodium hydroxide solution (20 mL) was added to a solution of Compound e: 5-fluoro-3-nitro-2-(2,2,2-trifluoroacetamido)benzoic acid (1.18 g, 4 mmol) dissolved in ethanol (20 mL). The reaction was warmed to 80° C. and stirred for 3 hrs. Ethanol was removed under reduced pressure, and the residue was adjusted to pH 4 with hydrochloric acid and filtered, to obtain Compound f: 2-amino-5-fluoro-3-nitrobenzoic acid as a yellow solid (0.72 g, yield 90%). MS (ESI) m/z: $[M-H]^-=199$.

Step 3: Preparation of methyl 2-amino-5-fluoro-3-nitrobenzoate

Thionyl chloride (2.38 g) was slowly added dropwise into a solution of Compound f: 2-amino-5-fluoro-3-nitrobenzoic acid (0.8 g, 4 mmol) dissolved in methanol (20 mL) while in an ice bath, warmed to reflux, and reacted for 8 hrs. After cooling, the solvent was removed under reduced pressure, and the residue was separated by flash column chromatography (petroleum ether:ethyl acetate=5:1) to obtain Compound g: methyl 2-amino-5-fluoro-3-nitrobenzoate as a yellow solid (0.5 g, yield 58%). MS (ESI) m/z: $[M+H]^+=215$.

Step 4: Preparation of methyl 2,3-diamino-5-fluorobenzoate

10% palladium on carbon (0.7 g) was added to a solution of Compound g: methyl 2-amino-5-fluoro-3-nitrobenzoate (7 g, 32.7 mmol) dissolved in methanol (50 mL), hydrogenated for 7 hrs at room temperature, and filtered. The residue was separated by flash column chromatography (petroleum ether:ethyl acetate=5:1) to obtain Compound h: methyl 2,3-diamino-5-fluorobenzoate as a yellow solid (2.16 g, yield 36%). MS (ESI) m/z: $[M+H]^+=185$.

Step 5: Preparation of methyl 6-fluoro-2-oxo-2,3-dihydro-1H-benzimidazole-4-carboxylate Analogous to the process in Step 1 in Preparation of Compound (1) in Example 1, Compound h: methyl 2,3-diamino-5-fluorobenzoate was cyclized with carbonyldiimidazole (CDI), to obtain Compound i: methyl 6-fluoro-2-oxo-2,3-dihydro-1H-benzimidazole-4-carboxylate (711 mg, yield 37%). MS (ESI) m/z: $[M+H]^+=211$.

Step 6: Preparation of methyl 2-chloro-6-fluoro-1H-benzimidazole-4-carboxylate Analogous to the process in Step 2 in Preparation of Compound (1) in Example 1, Compound i: methyl 6-fluoro-2-oxo-2,3-dihydro-1H-benzimidazole-4-carboxylate was chlorinated with phosphorus oxychloride, to obtain Compound j: methyl 2-chloro-6-fluoro-1H-benzimidazole-4-carboxylate (681 mg, yield 94%). MS (ESI) m/z: $[M+H]^+=229$.

Step 7: Preparation of methyl 6-fluoro-2-(piperazin-1-yl)-1H-benzimidazole-4-carboxylate Analogous to the process in Step 3 in Preparation of Compound (1) in Example 1, Compound j: methyl 2-chloro-6-fluoro-1H-benzimidazole-4-carboxylate was subjected to nucleophilic substitution with piperazine, to obtain Compound k: methyl 6-fluoro-2-(piperazin-1-yl)-1H-benzimidazole-4-carboxylate (430 mg, yield 65%). MS (ESI) m/z: $[M+H]^+=279$.

Step 8: Preparation of 6-fluoro-2-(piperazin-1-yl)-1H-benzimidazole-4-carboxamide To a solution of Compound k: methyl 6-fluoro-2-(piperazin-1-yl)-1H-benzimidazole-4-carboxylate (100 mg, 0.28 mmol) dissolved in tetrahydrofuran (5 mL), aqueous ammonia (5 mL) was added, warmed to 70° C., sealed, and reacted for 8 hrs. After cooling, the solvent was removed under reduced pressure, and the residue was separated by flash column chromatography (dichloromethane:methanol=10:1) to obtain Compound l: 6-fluoro-2-(piperazin-1-yl)-1H-benzimidazole-4-carboxamide as a white solid (20 mg, yield 28%). MS (ESI) m/z: $[M+H]^+=246$.

Step 9: Preparation of 6-fluoro-2-(4-(pyrimidin-4-yl)piperazin-1-yl)-1H-benzimidazole-4-carboxamide Analogous to the process in Step 5 in Preparation of Compound (1) in Example 1, Compound 1: 6-fluoro-2-

(piperazin-1-yl)-1H-benzimidazole-4-carboxamide was subjected to aromatic nucleophilic substitution with 4-chloropyrimidine, to obtain Compound (16): 6-fluoro-2-(4-(pyrimidin-4-yl)piperazin-1-yl)-1H-benzimidazole-4-carboxamide (21 mg, yield 48%). LC-MS (ESI): m/z 342 (M+1)$^+$. $^1$H NMR (300 MHz, DMSO-d6): δ 12.04 (br, 1H), 9.10 (br, 1H), 8.52 (s, 1H), 8.22 (d, 1H, J=7.2 Hz), 7.71 (br, 1H), 7.33-7.2 (m, 1H), 7.19-7.17 (m, 1H), 6.90 (d, 1H, J=7.2 Hz), 3.80 (br, 4H), 3.66 (br, 4H).

Example 17

Preparation of Compound (17): 6-fluoro-2-(4-(5-fluoropyrimidin-2-yl)piperazin-1-yl)-1H-benzimidazole-4-carboxamide

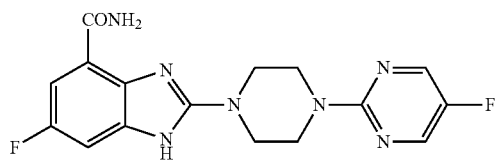

(17)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 2-chloro-5-fluoropyrimidine, to obtain Compound (17): 6-fluoro-2-(4-(5-fluoropyrimidin-2-yl)piperazin-1-yl)-1H-benzimidazole-4-carboxamide (27 mg, yield 87%). LC-MS (ESI): m/z 360 (M+1)$^+$. $^1$H NMR (300 MHz, DMSO-d6): δ 9.11 (br, 1H), 8.49 (s, 2H), 7.71-7.69 (m, 1H), 7.31-7.28 (m, 1H), 7.18-7.15 (m, 1H), 3.84-3.82 (m, 4H), 3.68-3.65 (m, 4H).

Example 18

Preparation of Compound (18): 2-(4-(5-(dimethylcarbamoyl)pyridin-2-yl)piperazin-1-yl)-6-fluoro-1H-benzimidazole-4-carboxamide

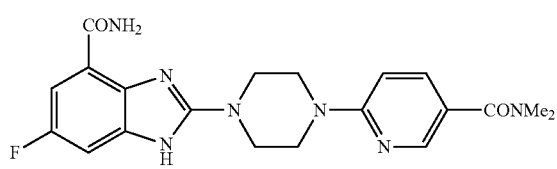

(18)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 6-chloro-3-dimethylcarbamoylpyridine, to obtain Compound (18): 2-(4-(5-(dimethylcarbamoyl)pyridin-2-yl)piperazin-1-yl)-6-fluoro-1H-benzimidazole-4-carboxamide (14 mg, yield 18%). LC-MS (ESI): m/z 412 (M+1)$^+$. $^1$H NMR (300 MHz, DMSO-d6): δ 12.57 (br, 1H), 9.12 (br, 1H), 8.23 (s, 1H), 7.70-7.63 (m, 2H), 7.31-7.27 (m, 1H), 7.18-7.14 (m, 1H), 6.94-6.91 (m, 1H), 3.72 (br, 8H), 2.95 (s, 6H).

Example 19

Preparation of Compound (19): 2-(4-(5-cyanopyrimidin-2-yl)piperazin-1-yl)-6-fluoro-1H-benzimidazole-4-carboxamide

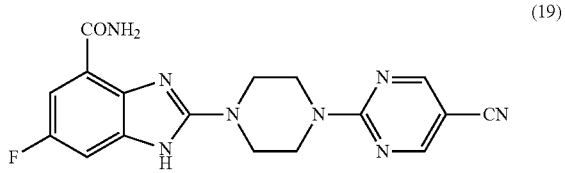

(19)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 2-chloro-5-cyanopyrimidine, to obtain Compound (19): 2-(4-(5-cyanopyrimidin-2-yl)piperazin-1-yl)-6-fluoro-1H-benzimidazole-4-carboxamide (43 mg, yield 77%). LC-MS (ESI): m/z 367 (M+1)$^+$. $^1$H NMR (300 MHz, DMSO-d6): δ 12.11 (br, 1H), 9.07 (br, 1H), 8.80 (s, 2H), 7.72 (br, 1H), 7.33-7.29 (m, 1H), 7.20-7.16 (m, 1H), 4.00 (br, 4H), 3.69 (br, 4H).

Example 20

Preparation of Compound (20): 6-fluoro-2-(4-(3-methylcarbamoylpyridin-2-yl)piperazin-1-yl)-1H-benzimidazole-4-carboxamide

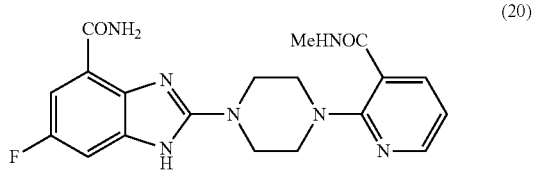

(20)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 2-chloro-N-methylnicotinamide, to obtain Compound (20): 6-fluoro-2-(4-(3-methylcarbamoylpyridin-2-yl)piperazin-1-yl)-1H-benzimidazole-4-carboxamide (28 mg, yield 52%). LC-MS (ESI): m/z 398 (M+1)$^+$. $^1$H NMR (300 MHz, DMSO-d6): δ 12.21 (br, 1H), 9.10 (br, 1H), 8.41 (br, 1H), 8.26-8.25 (m, 1H), 7.75-7.72 (m, 1H), 7.68 (br, 1H), 7.32-7.28 (m, 1H), 7.18-7.15 (m, 1H), 6.96-6.92 (m, 1H), 3.69 (br, 8H), 2.79 (s, 3H).

Example 21

Preparation of Compound (21): 6-fluoro-2-(4-(5-trifluoromethylpyridin-2-yl)piperazin-1-yl)-1H-benzimidazole-4-carboxamide

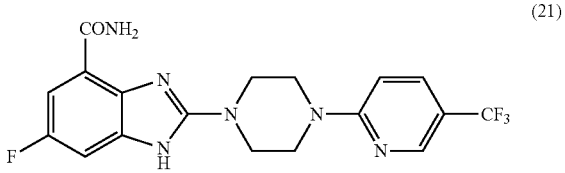 [SMILES: NC(=O)c1cc(F)cc2[nH]c(N3CCN(c4ccc(C(F)(F)F)cn4)CC3)nc12]

(21)

Analogous to the process in Step 5 in Preparation of Compound (1) in Example 1, Compound 1: 6-fluoro-2-

(piperazin-1-yl)-1H-benzimidazole-4-carboxamide was subjected to aromatic nucleophilic substitution with 2-chloro-5-trifluoromethylpyridine, to obtain Compound (21): 6-fluoro-2-(4-(5-trifluoromethylpyridin-2-yl)piperazin-1-yl)-1H-benzimidazole-4-carboxamide (23 mg, yield 52%). LC-MS (ESI): m/z 409 (M+1)+. $^1$H NMR (300 MHz, DMSO-d6): δ 12.32 (br, 1H), 9.10 (br, 1H), 8.44 (s, 1H), 7.85-7.81 (m, 1H), 7.70 (br, 1H), 7.32-7.28 (m, 1H), 7.19-7.15 (m, 1H), 7.06-7.02 (m, 1H), 3.81 (br, 4H), 3.70 (br, 4H).

Example 22

Preparation of Compound (22): 6-fluoro-2-(4-(5-methylcarbamoylpyrimidin-2-yl)piperazin-1-yl)-1H-benzimidazole-4-carboxamide

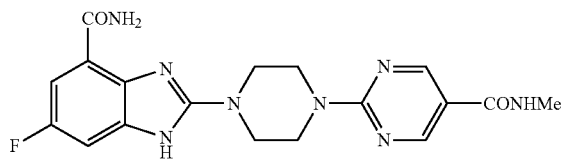

(22)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 2-chloro-N-methylpyrimidine-5-carboxamide, to obtain Compound (22): 6-fluoro-2-(4-(5-methylcarbamoylpyrimidin-2-yl)piperazin-1-yl)-1H-benzimidazole-4-carb oxamide (17 mg, yield 29%). LC-MS (ESI): m/z 399 (M+1)+. $^1$H NMR (300 MHz, DMSO-d6): δ 12.01 (br, 1H), 9.08 (br, 1H), 8.78 (s, 2H), 8.37 (br, 1H), 7.73 (br, 1H), 7.34-7.27 (m, 1H), 7.19-7.13 (m, 1H), 3.98 (br, 4H), 3.67 (br, 4H), 2.75 (s, 3H).

Example 23

Preparation of Compound (23): 6-fluoro-2-(4-(6-methylcarbamoylpyridazin-3-yl)piperazin-1-yl)-1H-benzimidazole-4-carboxamide

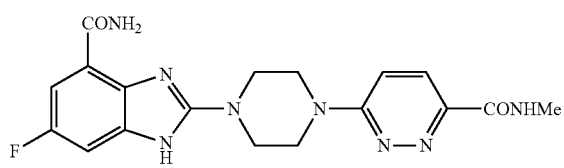

(23)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 6-chloro-N-methylpyridazin-3-carboxamide, to obtain Compound (23): 6-fluoro-2-(4-(6-methylcarbamoylpyridazin-3-yl)piperazin-1-yl)-1H-benzimidazole-4-carb oxamide (20 mg, yield 27%). LC-MS (ESI): m/z 399 (M+1)+. $^1$H NMR (300 MHz, DMSO-d6): δ 12.05 (br, 1H), 9.11 (br, 1H), 8.84 (br, 1H), 7.87 (d, 1H, J=10.5 Hz), 7.74 (br, 1H), 7.44-7.41 (m, 1H), 7.31 (d, 1H, J=10.5 Hz), 7.20-7.17 (m, 1H), 3.90 (br, 4H), 3.72 (br, 4H), 2.80 (s, 3H).

Example 24

Preparation of Compound (24): 6-fluoro-2-(4-(5-methylcarbamoylpyridin-2-yl)piperazin-1-yl)-1H-benzimidazole-4-carboxamide

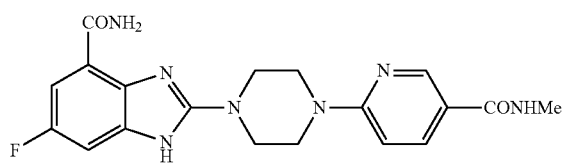

(24)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 6-chloro-N-methylnicotinamide, to obtain Compound (24): 6-fluoro-2-(4-(5-methylcarbamoylpyridin-2-yl)piperazin-1-yl)-1H-benzimidazole-4-carboxamide (6 mg, yield 13%). LC-MS (ESI): m/z 398 (M+1)+. $^1$H NMR (300 MHz, DMSO-d6): δ 12.58 (br, 1H), 9.12 (br, 1H), 8.62 (s, 1H), 8.04-7.98 (m, 1H), 7.72 (s, 1H), 7.32-7.26 (m, 2H), 7.17-7.15 (m, 1H), 6.98-6.92 (m, 1H), 3.75-3.69 (m, 8H), 2.73 (s, 3H).

Example 25

Preparation of Compound (25): 6-fluoro-2-(4-(5-methylcarbamoylpyrazin-2-yl)piperazin-1-yl)-1H-benzimidazole-4-carboxamide

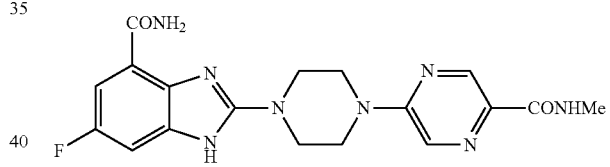

(25)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-chloro-N-methylpyrazin-2-carboxamide, to obtain Compound (25): 6-fluoro-2-(4-(5-methylcarbamoylpyrazin-2-yl)piperazin-1-yl)-1H-benzimidazole-4-carboxamide (38 mg, yield 64%). LC-MS (ESI): m/z 399 (M+1)+. $^1$H NMR (300 MHz, DMSO-d6): δ 12.05 (br, 1H), 9.09 (br, 1H), 8.62 (s, 1H), 8.39 (br, 1H), 8.34 (s, 1H), 7.72 (br, 1H), 7.33-7.29 (m, 1H), 7.19-7.17 (m, 1H), 3.88 (br, 4H), 3.70 (br, 4H), 2.77 (s, 3H).

Example 26

Preparation of Compound (26): 2-(4-(5-ethylcarbamoylpyrazin-2-yl)piperazin-1-yl)-6-fluoro-1H-benzimidazole-4-carboxamide

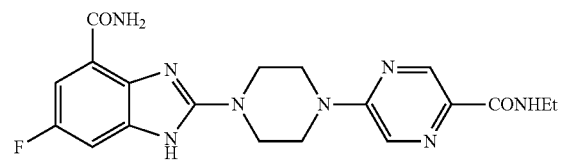

(26)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-chloro-N-ethylpyrazin-2-carboxamide, to obtain Compound (26): 2-(4-(5-ethylcarbamoylpyrazin-2-yl)piperazin-1-yl)-6-fluoro-1H-benzimidazole-4-carboxamide (19 mg, yield 31%). LC-MS (ESI): m/z 413 (M+1)$^+$. $^1$H NMR (300 MHz, DMSO-d6): δ 12.09 (br, 1H), 9.11 (br, 1H), 8.63 (s, 1H), 8.44-8.42 (m, 1H), 8.34 (s, 1H), 7.73 (br, 1H), 7.33-7.29 (m, 1H), 7.20-7.17 (m, 1H), 3.87 (br, 4H), 3.71 (br, 4H), 3.28 (q, 2H, J=6.9 Hz), 1.09 (t, 3H, J=6.9 Hz).

Example 27

Preparation of Compound (27): 6-fluoro-2-(4-(5-isopropylcarbamoylpyrazin-2-yl)piperazin-1-yl)-1H-benzimidazole-4-carboxamide (27)

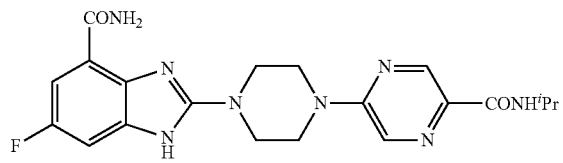

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-chloro-N-isopropylpyrazin-2-carboxamide, to obtain Compound (27): 6-fluoro-2-(4-(5-isopropylcarbamoylpyrazin-2-yl)piperazin-1-yl)-1H-benzimidazole-4-carboxamide (22 mg, yield 28%). LC-MS (ESI): m/z 427 (M+1)$^+$. $^1$H NMR (300 MHz, DMSO-d6): δ 12.04 (br, 1H), 9.09 (br, 1H), 8.63 (s, 1H), 8.32 (s, 1H), 8.05-8.00 (m, 1H), 7.70 (br, 1H), 7.34-7.29 (m, 1H), 7.20-7.16 (m, 1H), 4.09 (sep, 1H, J=6.6 Hz), 3.88 (br, 4H), 3.71 (br, 4H), 1.15 (d, 6H, J=6.6 Hz).

Example 28

Preparation of Compound (28): 2-(4-(5-t-butylcarbamoylpyrazin-2-yl)piperazin-1-yl)-6-fluoro-1H-benzimidazole-4-carboxamide (28)

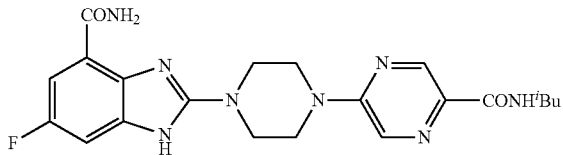

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-chloro-N-t-butylpyrazin-2-carboxamide, to obtain Compound (28): 2-(4-(5-t-butylcarbamoylpyrazin-2-yl)piperazin-1-yl)-6-fluoro-1H-benzimidazole-4-carboxamide (29 mg, yield 35%). LC-MS (ESI): m/z 441 (M+1)$^+$. $^1$H NMR (300 MHz, DMSO-d6): δ 12.04 (br, 1H), 9.09 (br, 1H), 8.62 (s, 1H), 8.31 (s, 1H), 7.71 (br, 1H), 7.53 (br, 1H), 7.33-7.29 (m, 1H), 7.20-7.16 (m, 1H), 3.86 (br, 4H), 3.71 (br, 4H), 1.37 (s, 9H).

Example 29

Preparation of Compound (29): 6-fluoro-2-(4-(5-(pyrrolin-1-acyl)pyrazin-2-yl)piperazin-1-yl)-1H-benzimidazole-4-carboxamide (29)

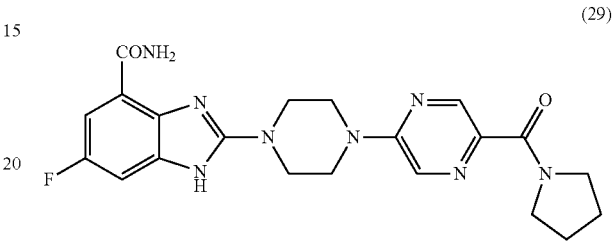

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with (5-chloropyrazin-2-yl)(pyrrolin-1-yl)methanone, to obtain Compound (29): 6-fluoro-2-(4-(5-(pyrrolin-1-acyl)pyrazin-2-yl)piperazin-1-yl)-1H-benzimidazole-4-carboxamide (14 mg, yield 17%). LC-MS (ESI): m/z 441 (M+1)$^+$. $^1$H NMR (300 MHz, DMSO-d6): δ 12.04 (br, 1H), 9.08 (br, 1H), 8.51 (s, 1H), 8.34 (s, 1H), 7.71 (br, 1H), 7.33-7.29 (m, 1H), 7.19-7.16 (m, 1H), 3.86 (br, 4H), 3.70 (br, 4H), 3.47-3.45 (m, 4H), 1.86-1.83 (m, 4H).

Example 30

Preparation of Compound (30): 6-fluoro-2-(4-(5-(morpholin-4-acyl)pyrazin-2-yl)piperazin-1-yl)-1H-benzimidazole-4-carboxamide (30)

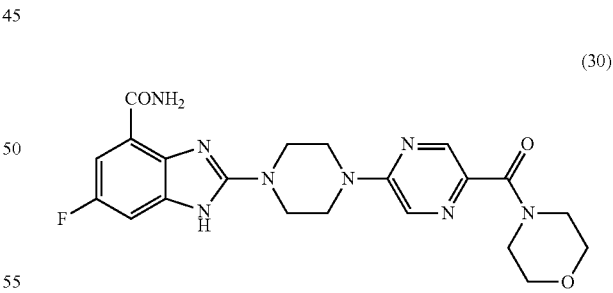

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with (5-chloropyrazin-2-yl)(morpholin-2-yl)methanone, to obtain Compound (30): 6-fluoro-2-(4-(5-(pyrrolin-1-acyl)pyrazin-2-yl)piperazin-1-yl)-1H-benzimidazole-4-carboxamide (32 mg, yield 37%). LC-MS (ESI): m/z 455 (M+1)$^+$. $^1$H NMR (300 MHz, DMSO-d6): δ 12.04 (br, 1H), 9.09 (br, 1H), 8.41 (s, 1H), 8.35 (s, 1H), 7.71 (br, 1H), 7.34-7.30 (m, 1H), 7.20-7.16 (m, 1H), 3.85 (br, 6H), 3.70 (br, 4H), 3.62 (br, 6H).

Example 31

Preparation of Compound (31): 6-fluoro-2-(4-(6-trifluoromethylpyridazin-3-yl)piperazin-1-yl)-1H-benzimidazole-4-carboxamide

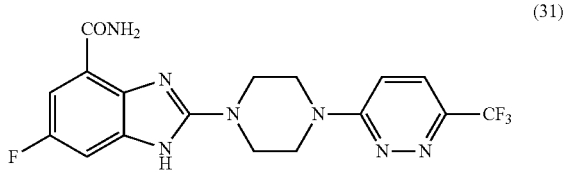
(31)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 3-chloro-6-trifluoromethylpyridazine, to obtain Compound (31): 6-fluoro-2-(4-(6-trifluoromethylpyridazin-3-yl)piperazin-1-yl)-1H-benzimidazole-4-carboxamide (15 mg, yield 20%). LC-MS (ESI): m/z 410 (M+1)$^+$. $^1$H NMR (300 MHz, DMSO-d6): δ 12.05 (br, 1H), 9.10 (br, 1H), 7.94-7.85 (m, 1H), 7.71 (br, 1H), 7.51-7.47 (m, 1H), 7.34-7.30 (m, 1H), 7.21-7.17 (m, 1H), 3.93 (br, 4H), 3.72 (br, 4H).

Example 32

Preparation of Compound (32): 6-fluoro-2-(4-(6-trifluoromethylpyridine-3-yl)piperazin-1-yl)-1H-benzimidazole-4-carboxamide

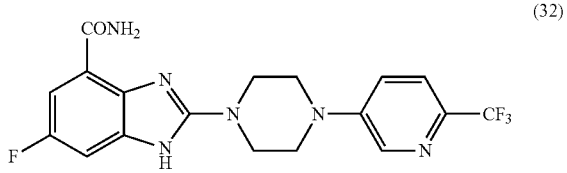 [SMILES: NC(=O)c1cc(F)cc2[nH]c(N3CCN(c4ccc(C(F)(F)F)nc4)CC3)nc12]
(32)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-bromo-2-trifluoromethylpyridine, to obtain Compound (32): 6-fluoro-2-(4-(6-trifluoromethylpyridine-3-yl)piperazin-1-yl)-1H-benzimidazole-4-carboxamide (23 mg, yield 19%). LC-MS (ESI): m/z 409 (M+1)$^+$. $^1$H NMR (300 MHz, DMSO-d6): δ 9.09 (br, 1H), 8.50 (s, 1H), 7.72-7.66 (m, 2H), 7.52-7.48 (m, 1H), 7.33-7.28 (m, 1H), 7.20-7.16 (m, 1H), 3.72 (br, 4H), 3.54 (br, 4H).

Example 33

Preparation of Compound (33:) 6-fluoro-2-(4-(2-trifluoromethylpyrimidin-5-yl)piperazin-1-yl)-1H-benzimidazole-4-carboxamide

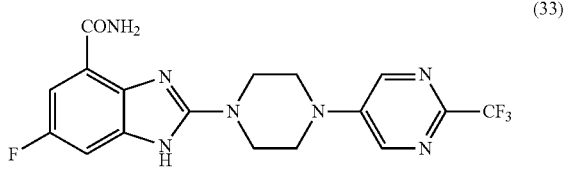 [SMILES: NC(=O)c1cc(F)cc2[nH]c(N3CCN(c4cnc(C(F)(F)F)nc4)CC3)nc12]
(33)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-bromo-2-trifluoromethylpyrimidine, to obtain Compound (33): 6-fluoro-2-(4-(2-trifluoromethylpyrimidin-5-yl)piperazin-1-yl)-1H-benzimidazole-4-carboxamide (12 mg, yield 16%). LC-MS (ESI): m/z 410 (M+1)$^+$. $^1$H NMR (300 MHz, DMSO-d6): δ 12.04 (br, 1H), 9.09 (br, 1H), 8.69 (s, 2H), 7.71 (br, 1H), 7.32-7.29 (m, 1H), 7.20-7.17 (m, 1H), 3.73 (br, 4H), 3.62 (br, 4H).

Example 34

Preparation of Compound (34): 6-fluoro-2-(4-(5-trifluoromethylpyrimidin-2-yl)piperazin-1-yl)-1H-benzimidazole-4-carboxamide

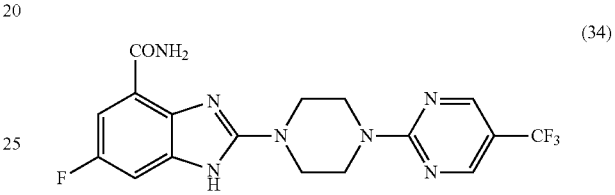
(34)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 2-chloro-5-trifluoromethylpyrimidine, to obtain Compound (34): 6-fluoro-2-(4-(5-trifluoromethylpyrimidin-2-yl)piperazin-1-yl)-1H-benzimidazole-4-carboxamide (8 mg, yield 14%). LC-MS (ESI): m/z 410 (M+1)$^+$. $^1$H NMR (300 MHz, DMSO-d6): δ 12.02 (br, 1H), 9.09 (br, 1H), 8.75 (s, 2H), 7.72 (br, 1H), 7.33-7.29 (m, 1H), 7.20-7.17 (m, 1H), 4.00 (br, 4H), 3.69 (br, 4H).

Example 35

Preparation of Compound (35): 6-fluoro-2-(4-(5-trifluoromethylpyrazin-2-yl)piperazin-1-yl)-1H-benzimidazole-4-carboxamide

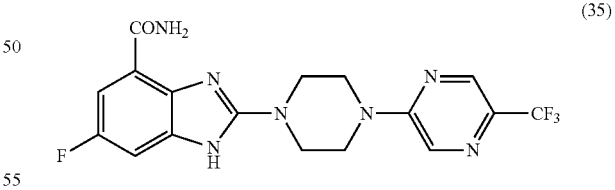
(35)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 2-chloro-5-trifluoromethylpyrazine, to obtain Compound (35): 6-fluoro-2-(4-(5-trifluoromethylpyrazin-2-yl)piperazin-1-yl)-1H-benzimidazole-4-carboxamide (60 mg, yield 90%). LC-MS (ESI): m/z 410 (M+1)$^+$. $^1$H NMR (300 MHz, DMSO-d6): δ 12.04 (br, 1H), 9.09 (br, 1H), 8.51 (s, 1H), 8.50 (s, 1H), 7.71 (br, 1H), 7.33-7.30 (m, 1H), 7.20-7.17 (m, 1H), 3.89 (br, 4H), 3.71 (br, 4H).

Example 36

Preparation of Compound (36): 2-(4-(5-dimethyl-carbamoylpyrazin-2-yl)piperazin-1-yl)-6-fluoro-1H-benzimidazole-4-carboxamide

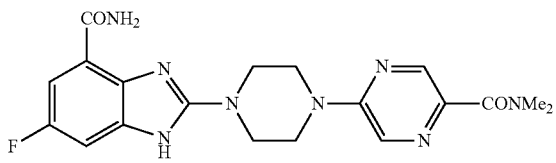

(36)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-chloro-N,N-dimethylpyrazin-2-carboxamide, to obtain Compound (36): 2-(4-(5-dimethylcarbamoylpyrazin-2-yl)piperazin-1-yl)-6-fluoro-1H-benzimidazole-4-carb oxamide (29 mg, yield 37%). LC-MS (ESI): m/z 413 (M+1)$^+$. $^1$H NMR (300 MHz, DMSO-d6): δ 12.02 (br, 1H), 9.09 (br, 1H), 8.37 (s, 1H), 8.34 (s, 1H), 7.71 (br, 1H), 7.33-7.30 (m, 1H), 7.20-7.16 (m, 1H), 3.83 (br, 4H), 3.73 (br, 1H), 3.07 (s, 3H), 2.98 (s, 3H).

Example 37

Preparation of Compound (37): 2-(4-(5-cyanopy-razin-2-yl)piperazin-1-yl)-6-fluoro-1H-benzimidazole-4-carboxamide

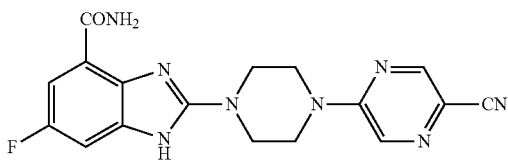

(37)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-chloro-2-cyanopyrazine, to obtain Compound (37): 2-(4-(5-cyanopyrazin-2-yl)piperazin-1-yl)-6-fluoro-1H-benzimidazole-4-carboxamide (40 mg, yield 58%). LC-MS (ESI): m/z 367 (M+1)$^+$. $^1$H NMR (300 MHz, DMSO-d6): δ 12.05 (br, 1H), 9.07 (br, 1H), 8.59 (s, 1H), 8.49 (s, 1H), 7.69 (s, 1H), 7.33-7.29 (m, 1H), 7.20-7.16 (m, 1H), 3.93 (br, 4H), 3.71 (br, 4H).

Example 38

Preparation of Compound (38): 2-(4-(2-cyanopy-rimidin-5-yl)piperazin-1-yl)-6-fluoro-1H-benzimidazole-4-carboxamide

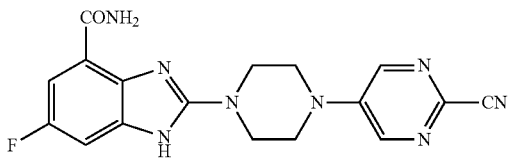

(38)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-bromo-2-cyanopyrimidine, to obtain Compound (38): 2-(4-(2-cyanopyrimidin-5-yl)piperazin-1-yl)-6-fluoro-1H-benzimidazole-4-carboxamide (18 mg, yield 26%). LC-MS (ESI): m/z 367 (M+1)$^+$. $^1$H NMR (300 MHz, DMSO-d6): δ 12.03 (br, 1H), 9.08 (br, 1H), 8.63 (s, 2H), 7.73-7.65 (m, 1H), 7.33-7.29 (m, 1H), 7.22-7.17 (m, 1H), 3.73-3.69 (m, 8H).

Example 39

Preparation of Compound (39): 6-fluoro-2-(4-(2-methylcarbamoylpyrimidin-2-yl)piperazin-5-yl)-1H-benzimidazole-4-carboxamide

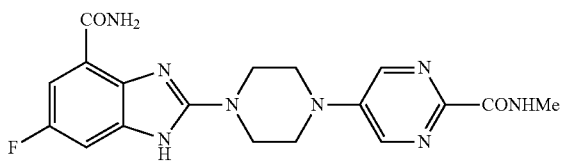

(39)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-bromo-N-methylpyrimidine-2-carboxamide, to obtain Compound (39): 6-fluoro-2-(4-(2-methylcarbamoylpyrimidin-2-yl)piperazine-5-yl)-1H-benzimidazole-4-carboxamide (16 mg, yield 29%). LC-MS (ESI): m/z 399 (M+1)$^+$. $^1$H NMR (300 MHz, DMSO-d6): δ 12.02 (br, 1H), 9.08 (br, 1H), 8.67 (s, 2H), 8.34 (br, 1H), 7.71 (br, 1H), 7.33-7.27 (m, 1H), 7.19-7.12 (m, 1H), 3.99 (br, 4H), 3.68 (br, 4H), 2.72 (s, 3H).

Example 40

Preparation of Compound (40): 2-(4-(2-ethylcar-bamoylpyrimidin-5-yl)piperazin-1-yl)-6-fluoro-1H-benzimidazole-4-carboxamide

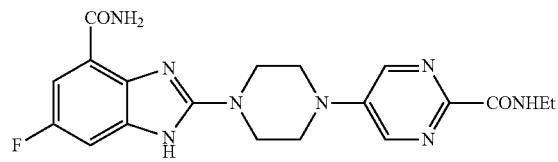

(40)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-bromo-N-ethylpyrimidine-2-carboxamide, to obtain Compound (40): 2-(4-(2-ethylcarbamoylpyrimidin-5-yl)piperazin-1-yl)-6-fluoro-1H-benzimidazole-4-carboxamide (17 mg, yield 23%). LC-MS (ESI): m/z 413 (M+1)$^+$. $^1$H NMR (300 MHz, DMSO-d6): δ 12.01 (br, 1H), 9.09 (br, 1H), 8.64 (s, 2H), 8.31 (br, 1H), 7.72 (br, 1H), 7.34-7.27 (m, 1H), 7.19-7.13 (m, 1H), 3.96 (br, 4H), 3.65 (br, 4H), 3.26 (q, 2H, J=6.9 Hz), 1.07 (t, 3H, J=6.9 Hz).

Example 41

Preparation of Compound (41): 2-(4-(2-dimethyl-carbamoylpyrimidin-5-yl)piperazin-1-yl)-6-fluoro-1H-benzimidazole-4-carboxamide

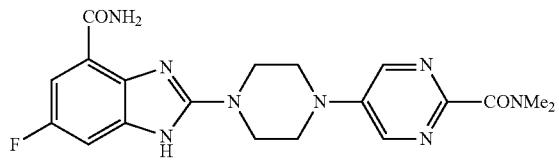

(41)

Analogous to the process in Step 5 in Preparation of Compound (1) in Example 1, Compound 1: 6-fluoro-2-(piperazin-1-yl)-1H-benzimidazole-4-carboxamide was subjected to aromatic nucleophilic substitution with 5-bromo-N-dimethylpyrimidin-2-carboxamide, to obtain Compound (41): 2-(4-(2-dimethylcarbamoylpyrimidin-5-yl)piperazin-1-yl)-6-fluoro-1H-benzimidazole-4-carboxamide (19 mg, yield 26%). LC-MS (ESI): m/z 413 (M+1)$^+$. $^1$H NMR (300 MHz, DMSO-d6): δ 12.03 (br, 1H), 9.07 (br, 1H), 8.63 (s, 2H), 8.32 (br, 1H), 7.72 (br, 1H), 7.31-7.26 (m, 1H), 7.18-7.13 (m, 1H), 3.97 (br, 4H), 3.67 (br, 4H), 3.08 (s, 3H), 2.97 (s, 3H).

Biological Evaluation

Experimental Principle

Poly(ADP-ribosyl)ation of nuclear proteins is a post-translational modification occurred in response to DNA damage. PARP is the abbreviation of poly(ADP-ribose) polymerase, which catalyzes the attachment of poly(ADP-ribose) to an adjacent nuclear protein in the presence of NAD, thus eliciting a mechanism of DNA repair through base excision repair pathway. The level of biotin-labeled ADP-ribose binding to histone can be detected by using the HT Universal Chemiluminescent PARP Assay Kit commercially available from Trevigen Corp.

Reagents and Materials

1. HT Universal Chemiluminescent PARP Assay Kit with Histone-coated Strip Wells, commercially available from Trevigen (US), Catalog #: 4676-096-K.

2. Plate reader: EnVision Multilabel Plate Reader available from Perkin Elmer (US).

Solutions and Buffers

1. Washing buffer: 0.1% Triton X-100 in PBS.

2. 20×PARP buffer—It was 1:20 diluted in deionized water to obtain a 1× buffer, which was used for diluting the recombinant PARP enzyme, PARP Cocktails, and test compounds.

3. 10×PARP Cocktail was formulated into a 1×PARP Cocktail by mixing 10×PARP Cocktail 2.5 μl/well, 10× activated DNA 2.5 μl/well, and 1×PARP buffer 20 μl/well.

4. The PARP enzyme was carefully diluted with the 1×PARP buffer just before use, the diluted enzyme solution should be used as quickly as possible and the remaining solution should be discarded.

5. Strep-HRP was 1:500 diluted with the 1× Strep diluent just before use to obtain a 1× solution.

6. The chemiluminescent substrate was prepared just before use, by uniformly mixing equal volume of Peroxy-Glow A and B to obtain a substrate for horseradish peroxidase.

Experimental Method

Formulation of Compound Solutions 1. 10 mM stock solution of each test compound was diluted to 10 μM, and 1 μM in DMSO.

2. Just before experiment, the solution at various concentration gradients of each compound dissolved in DMSO was 1:20 diluted in the 1×PARP buffer, to obtain a 5× compound solution for test. The positive and negative control wells contained the 1×PARP buffer (containing 5% DMSO).

Experimental Procedures 1. 50 μl of 1×PARP buffer per well was added to infiltrate the histone, and the plate was incubated for 30 min at room temperature. Then the 1×PARP buffer in each well was aspirated, and the remaining liquid was tapped dry on paper towels.

2. The diluted 5× solutions of Compounds (1) to (37) were added to respective wells (10 μl per well). The positive and negative control wells contained the 1×PARP buffer (containing 5% DMSO).

3. The PARP enzyme was diluted in the 1×PARP buffer to give a concentration of 0.5 Unit per 15 μl, and then 15 μl of the enzyme solution was added to each well except that the negative control well was added exclusively with the 1×PARP buffer. The plate was incubated for 10 min at room temperature.

4. 25 μl of the 1×PARP Cocktail was sequentially added to each well.

5. The plate was incubated for 60 min at 27° C.

6. After incubation, the reaction solution was aspirated from the wells, and the remaining liquid was tapped dry on paper towels. Then, the plate was washed 4 times with 0.1% Triton X-100 in PBS (200 μl per well per wash), and the remaining liquid was tapped dry on paper towels.

7. Subsequently, the diluted 1× Strep-HRP solution was added to each well, and then the plate was incubated for 60 min at 27° C.

8. After incubation, the reaction solution was aspirated from the wells, and the remaining liquid was tapped dry on paper towels. Then, the plate was washed 4 times with 0.1% Triton X-100 in PBS (200 μl per well per wash), and the remaining liquid was tapped dry on paper towels.

9. After washing, equal volume of the PeroxyGlow A and B solutions were uniformly mixed, 100 μl of the solution was added to each well, and the chemiluminescent signals were recorded on a plate reader immediately.

Data Processing

The readout of each well is converted into the percent inhibition. The percent inhibition of the compounds may be calculated by an equation below:

$$\text{Inhibition}(\%) = \frac{\text{Readout of positive control well} - X}{\text{Readout of positive control well} - \text{Readout of negative control well}} \times 100\%$$

Note: the readout of the positive control well is designated as 100% enzyme activity; the readout of the negative control well is designated as 0% enzyme activity; and the activity X refers to the readout from respective concentration of each sample.

TABLE 1

Inhibition of the compounds on PARP-1 enzyme

| Compound No | Inhibition (%) at 100 nM | Inhibition (%) at 30 nM | IC$_{50}$ |
|---|---|---|---|
| (1) | 76 | 59 | 48 nM |
| (2) | 69 | 42 | 49 nM |
| (3) | 13 | 6 | 3579 nM |
| (4) | 53 | 27 | 106 nM |

TABLE 1-continued

Inhibition of the compounds on PARP-1 enzyme

| Compound No | Inhibition (%) at 100 nM | Inhibition (%) at 30 nM | IC$_{50}$ |
|---|---|---|---|
| (5) | 60 | 32 | 74 nM |
| (6) | 54 | 26 | 98 nM |
| (7) | 85 | 73 | 17 nM |
| (8) | 16 | 8 | 928 nM |
| (9) | 31 | 16 | 217 nM |
| (10) | 64 | 38 | 55 nM |
| (11) | 78 | 59 | 25 nM |
| (12) | 77 | 57 | 25 nM |
| (13) | 69 | 43 | 49 nM |
| (14) | 78 | 57 | 28 nM |
| (15) | 70 | 44 | 54 nM |
| (16) | 91 | 78 | 9 nM |
| (17) | 78 | 56 | 26 nM |
| (18) | 77 | 56 | 30 nM |
| (19) | 93 | 77 | 9 nM |
| (20) | 67 | 39 | 48 nM |
| (21) | 60 | 32 | 68 nM |
| (22) | 93 | 71 | 10 nM |
| (23) | 89 | 78 | 12 nM |
| (24) | 65 | 45 | 45 nM |
| (25) | 92 | 79 | 7 nM |
| (26) | 94 | 80 | 7 nM |
| (27) | 86 | 66 | 14 nM |
| (28) | 78 | 53 | 25 nM |
| (29) | 88 | 71 | 12 nM |
| (30) | 92 | 78 | 9 nM |
| (31) | 95 | 80 | 8 nM |
| (32) | 84 | 66 | 15 nM |
| (33) | 98 | 88 | 5 nM |
| (34) | 60 | 36 | 56 nM |
| (35) | 91 | 76 | 9 nM |
| (36) | 92 | 83 | 8 nM |
| (37) | 98 | 87 | 3 nM |
| (38) | 95 | 84 | 6 nM |
| (39) | 92 | 78 | 9 nM |
| (40) | 93 | 77 | 9 nM |
| (41) | 92 | 75 | 8 nM |

The data given in Table 1 fully suggests that the compounds of the present invention are all PARP-1 inhibitors. As indicated in the examples, the IC$_{50}$ value of Compounds (1), (2), (5), (6), (7), (10), (11), (12), (13), (14), (15), (16), (17), (18), (19), (20), (21), (22), (23), (24), (25), (26), (27), (28), (29), (30), (31), (32), (33), (34), (35), (36), (37), (38), (39), (40), and (41) is not greater than 100 nM, and the IC$_{50}$ value of Compounds (16), (19), (25), (26), (30), (31), (33), (35), (36), (37), (38), (39), (40), and (41) is further not greater than 10 nM.

What is claimed is:

1. A benzimidazole-2-piperazine heterocyclic compound or a pharmaceutically acceptable salt thereof, wherein the benzimidazole-2-piperazine heterocyclic compound is selected from the group consisting of Compounds below:

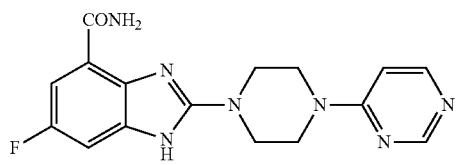
(16)

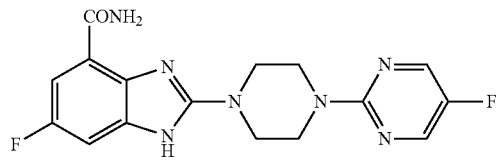
(17)

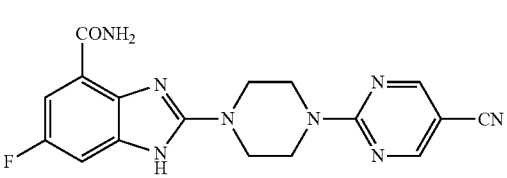
(19)

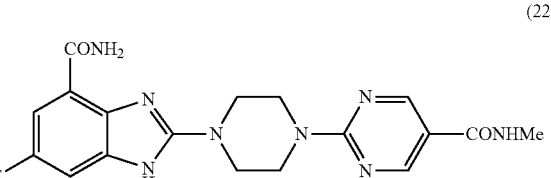
(22)

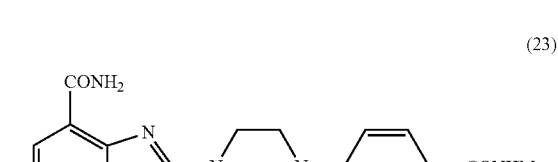
(23)

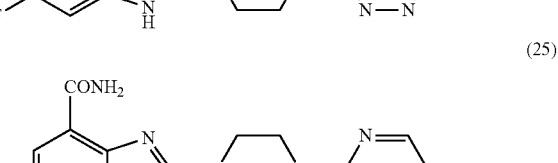
(25)

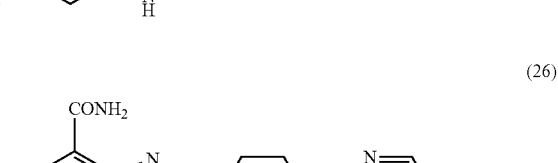
(26)

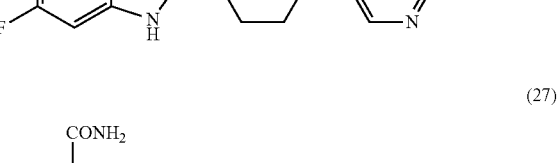
(27)

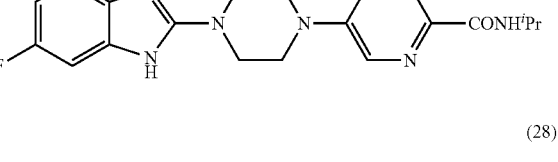
(28)

-continued

(29)
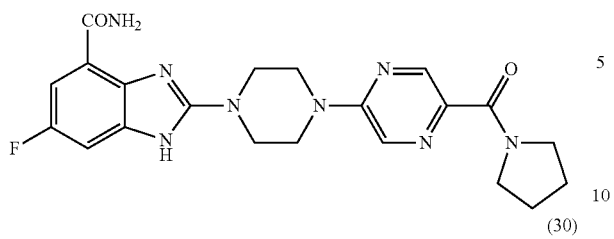

(30)
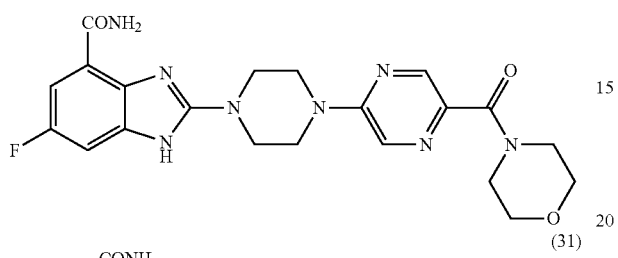

(31)
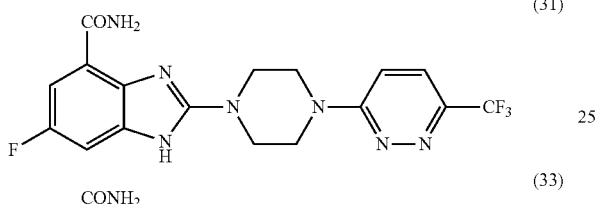

(33)
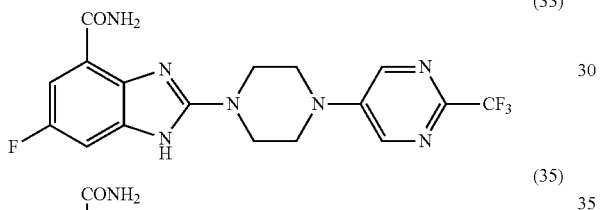

(35)
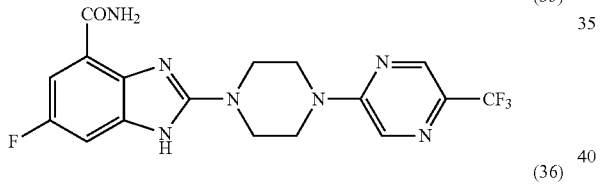

(36)
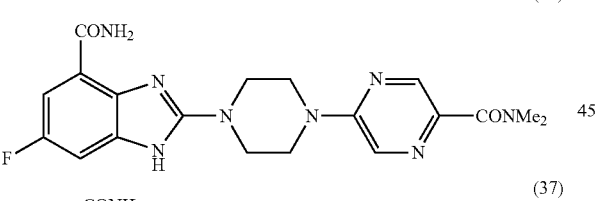

(37)
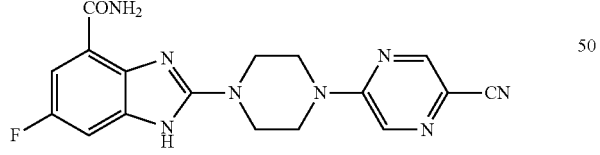

-continued

(38)
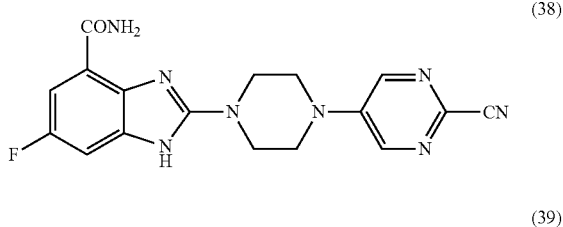

(39)
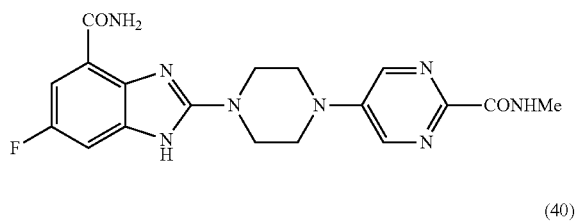

(40)
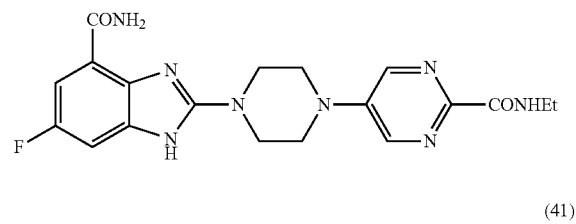

(41)
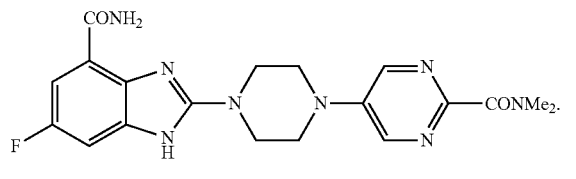

2. The benzimidazole-2-piperazine heterocyclic compound according to claim 1, wherein the pharmaceutically acceptable salt is a hydrochloride, a sulfate, a phosphate, an acetate, a trifluoroacetate, a methanesulfonate, a trifluoromethanesulfonate, a p-toluenesulfonate, a tartrate, a maleate, a fumarate, a succinate or a malate of the compound.

3. A pharmaceutical composition, comprising a therapeutically effective amount of the compound of claim 1 or a pharmaceutically acceptable salt thereof as the active ingredient and one or more pharmaceutically acceptable carriers and/or diluents.

4. The pharmaceutical composition according to claim 3, which is prepared into tablets, capsules, an aqueous suspension, an oily suspension, a dispersible powder, granules, lozenges, an emulsion, a syrup, a cream, an ointment, a suppository, or an injection.

\* \* \* \* \*